United States Patent
Hakonarson et al.

(10) Patent No.: US 9,790,550 B2
(45) Date of Patent: Oct. 17, 2017

(54) ASTHMA SUSCEPTIBILITY LOCI LOCATED AT CHROMOSOME 1Q31 FOR USE IN DIAGNOSTIC AND THERAPEUTIC METHODS

(75) Inventors: Hakon Hakonarson, Malvern, PA (US); Patrick M. A. Sleiman, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 26 days.

(21) Appl. No.: 12/992,965

(22) PCT Filed: May 18, 2009

(86) PCT No.: PCT/US2009/044412
§ 371 (c)(1),
(2), (4) Date: Apr. 29, 2011

(87) PCT Pub. No.: WO2009/140699
PCT Pub. Date: Nov. 19, 2009

(65) Prior Publication Data
US 2011/0200583 A1    Aug. 18, 2011

Related U.S. Application Data

(60) Provisional application No. 61/053,808, filed on May 16, 2008.

(51) Int. Cl.
| | | |
|---|---|---|
| C07H 21/02 | (2006.01) | |
| C07H 21/04 | (2006.01) | |
| *C12Q 1/68* | (2006.01) | |
| C12P 19/34 | (2006.01) | |

(52) U.S. Cl.
CPC ..... *C12Q 1/6883* (2013.01); *C12Q 2600/136* (2013.01); *C12Q 2600/156* (2013.01); *C12Q 2600/158* (2013.01)

(58) Field of Classification Search
CPC .................. C12Q 1/6878; C12Q 2600/156
See application file for complete search history.

(56) References Cited

U.S. PATENT DOCUMENTS

2001/0053519 A1* 12/2001 Fodor et al. ................ 435/6
2006/0014165 A1  1/2006 Hakonarson et al.

OTHER PUBLICATIONS dbSNP Submitted SNP(ss) Details: ss70751518, rs2786098 (Apr. 20, 2007), from www.ncbi.nlm.nih.gov, p. 1.*
GenBank Locus BC063877 '*Homo sapiens* DENN/MADD domain containing 1B, mRNA' (Sep. 9, 2005) from www.ncbi.nlm.nih.gov, pp. 1-4.*
Gunderson K.L. et al. Pharmacogenomics Jun. 2006, vol. 7, No. 4, pp. 641-648.*
Reference SNP(refSNP) Cluster Report: rs2821132, from www.ncbi.nlm.nih.gov, pp. 1-3, printed Jul. 22, 2013.*
Reference SNP(refSNP) Cluster Report: rs2476019, from www.ncbi.nlm.nih.gov, pp. 1-3, printed Jul. 22, 2013.*
Reference SNP(refSNP) Cluster Report: rs2759661, from www.ncbi.nlm.nih.gov, pp. 1-3, printed Jul. 22, 2013.*
Larin Z. et al. Nucleic Acids Research, 1994, vol. 22, No. 18, pp. 3689-3692.*
Anderson R.C. et al. "Polynucleotide Arrays for Genetic Sequence Analysis" in Topics in Current Chemistry,vol. 194 (1998), pp. 117-129.*
Macewan, D.J. "TNF ligands and receptors—a matter of life and death." Br J Pharmacol. Feb. 2002;135(4):855-75.
NCBI Entrez Single Nucleotide Polymorphism entry rs2477077 [Retrieved from the Internet on Sep. 15, 2009: <http://www.ncbi.mln/nih.gov/SNP/snp_ref.cgi?searchType=adhoc_search&type=rs&rs=rs2477077> May 25, 2006 (May 25, 2006); p. 1.

* cited by examiner

Primary Examiner — Stephen Kapushoc
(74) Attorney, Agent, or Firm — Kathleen D. Rigaut; Dann, Dorfman, Herrell & Skillman

(57) ABSTRACT

Methods and composition are provided for diagnosing pediatrıc onset asthma based on the single nucleotide polymorphism on chromosome 1q31 wherein said single nucleotide polymorphism is set forth in Table 2 or Table 6 of the instant invention Method and composition are also provided for treating and preventing asthma or other inflammatory conditions in a patient in need thereof comprısing administering an effective amount of an at least one inhibitor which reduces the expression of DENND1 B gene product.

3 Claims, 7 Drawing Sheets

ASTHMA SUSCEPTIBILITY LOCI LOCATED AT CHROMOSOME 1Q31 FOR USE IN DIAGNOSTIC AND THERAPEUTIC METHODS

This application is a §371 national phase entry of PCT/US2009/044412 filed May 18, 2009, which claims priority to U.S. Provisional Application 61/053,808 filed May 16, 2008, the entire contents of which is incorporated herein by reference.

FIELD OF THE INVENTION

This invention relates to the fields of airway disease and genetic testing. More specifically, the invention provides compositions and methods for the diagnosis and treatment of asthma and other allergic conditions.

BACKGROUND OF THE INVENTION

Several publications and patent documents are cited throughout the specification in order to describe the state of the art to which this invention pertains. Each of these citations is incorporated by reference herein as though set forth in full.

Asthma is a heterogeneous and multifactorial disease that manifests as episodes of wheezing, coughing and shortness of breath. Both family-based and twin studies indicate that asthma is a complex genetic disorder[1]. Multiple genetic and environmental factors are also known to modulate the clinical expression of the disease and its associated phenotypes, bronchial hyper-responsiveness, atopy, and elevated IgE[2,3]. In a recent GWA study, a single locus harboring ORMDL3 on 17q12-q21 was found to associate with asthma contributing modestly to disease risk, thereby notably reducing the possibility of the presence of common variants with large effect size in asthma[6]. However, as only a small proportion of the disease heritability has been explained to date, it follows that additional high frequency variants of modest risk remain to be uncovered. The identification of further genetic predisposition loci may lead to improved understanding of the biological basis of the disease and potentially also serve as new therapeutic targets.

GWA has proven to be a robust approach to gene variant discovery in complex disease[7]. However, unlike type 2 diabetes or inflammatory bowel disease (IBD) where multiple variants underlying the genetic susceptibility to these conditions have been discovered[8,9], only a single locus has thus far been shown to associate with asthma predisposition through GWA[6]. This suggests that either substantially larger numbers of subjects need to be studied, as with type 2 diabetes and IBD, or the sample must be enriched for genetic disease by sampling for lower age of onset or increased disease severity. Age of onset is one of the most easily tractable asthma phenotypes and, as longitudinal studies have established, strongly correlated with a number of other asthma phenotypes[4,5].

Clearly a need exists to identify other genes involved in the manifestation of the asthmatic phenotype, particularly pediatric onset asthma. Such knowledge will facilitate diagnosis of this condition as well as provide new targets for the development of potent therapeutics for the treatment of asthma.

SUMMARY OF THE INVENTION

In accordance with the present invention, compositions and methods are provided for diagnosis and treatment of asthma. An exemplary method entails detecting the presence of at least one genetic alteration, e.g., a single nucleotide polymorphism, on chromosome 1q31 in a target polynucleotide wherein if the single nucleotide polymorphism is present, the patient has an increased risk for developing asthma. Exemplary single nucleotide polymorphisms associated with the development of asthma include, without limitation, those disclosed in the Tables hereinbelow. Such pediatric onset associated genetic alterations may also be detected in the linkage disequilibrium block present between positions 193434182 (rs 2284664) and 195052641 on chromosome 1.

The methods of the invention can include alternative means for detecting the disclosed genetic alterations and polymorphisms. For example, such methods of detection can further comprises processes such as specific hybridization, measurement of allele size, restriction fragment length polymorphism analysis, allele-specific hybridization analysis, single base primer extension reaction, and sequencing of an amplified polynucleotide.

In a preferred embodiment, the polymorphism is on chromosome 1q31 and is provided in Tables 2 and 6.

In yet another aspect, nucleic acid molecules useful for amplifying the nucleic acids encoding the single nucleotide polymorphisms disclosed herein are provided. Also provided are solid supports comprising suitable nucleic acid targets to facilitate detection of such SNPS in patient samples. A suitable solid support for this process includes a microarray.

Finally, the invention also encompasses screening methods to identify agents which modulate the aberrant IgE production, brochoconstriction and airway inflammation observed in the asthma-associated SNP containing cells described herein. An exemplary method entails providing cells comprising at least one of the SNPs disclosed in Table 1; providing cells which express these gene(s) which lack the cognate polymorphisms (step b); contacting each cell type with a test agent and analyzing whether said agent alters parameters associated with the asthmatic phenotype. Agents so identified are also within the scope of the invention. Exemplary agents for down-modulating the expression of the DENND1B gene include siRNA molecules which are provided below in Table 13. Such siRNA should have efficacy for the treatment of asthma and may be used alone or in combination with agents conventionally used to treat this disease.

Also provided are transgenic mice comprising the SNP containing nucleic acid molecules described herein. Such mice provide a superior in vivo screening tool to identify agents which modulate the progression and development of asthma.

DETAILED DESCRIPTION OF THE INVENTION

Figure 1:
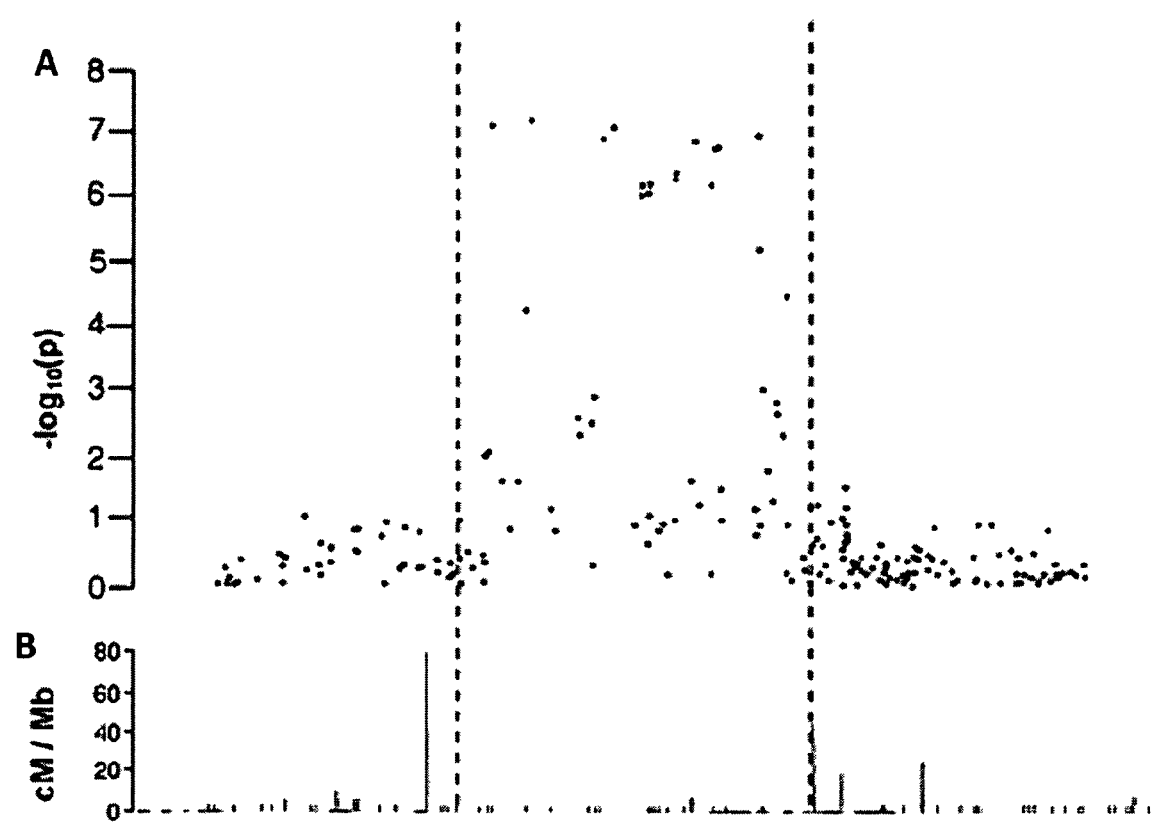
FIG. 1: Representation of the chromosome 1q31 associated interval. Panel A: Scatter plot of the $\log_{10}$ P values plotted by base pair. Common coordinates for the X-axis are given at the bottom of the figure. Panel B: Recombination rate around the associated interval. Dashed black lines across panels A and B represent demarcation of the associated interval where p-values and odds ratios return to background levels. Panel C: Location of the CRB1 and DENND1B genes and the associated SNPs in relation to these genes, all SNPs were intergenic or intronic. Panel D: LD plot of the $r^2$ values in CHOP AA control samples. Panel E: LD plot of the $r^2$ values in the CHOP EA control samples.
Figure 1:
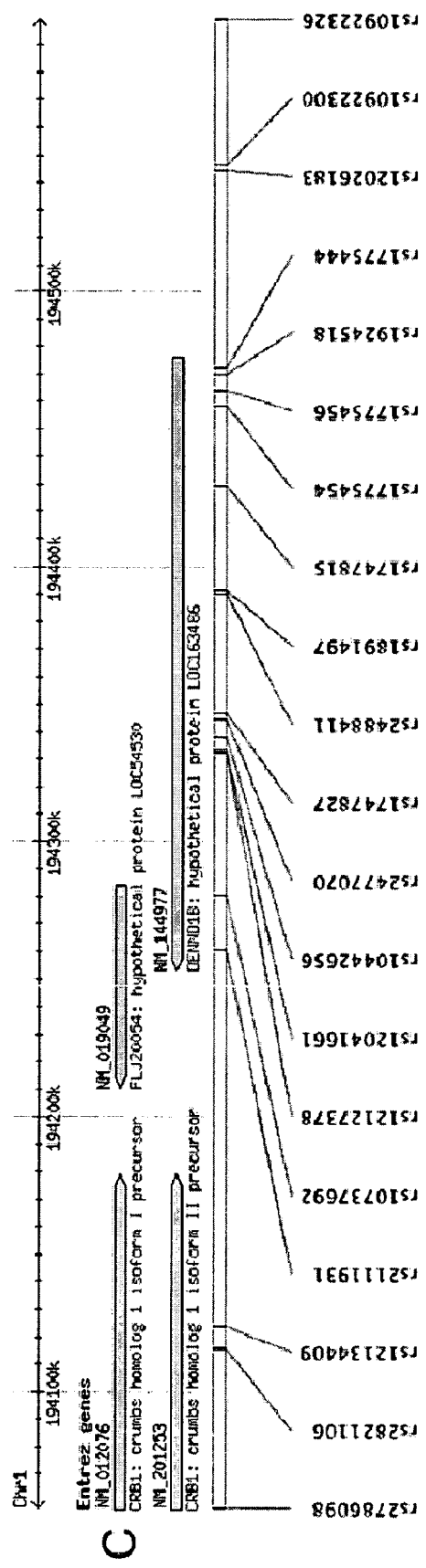
Figure 1:
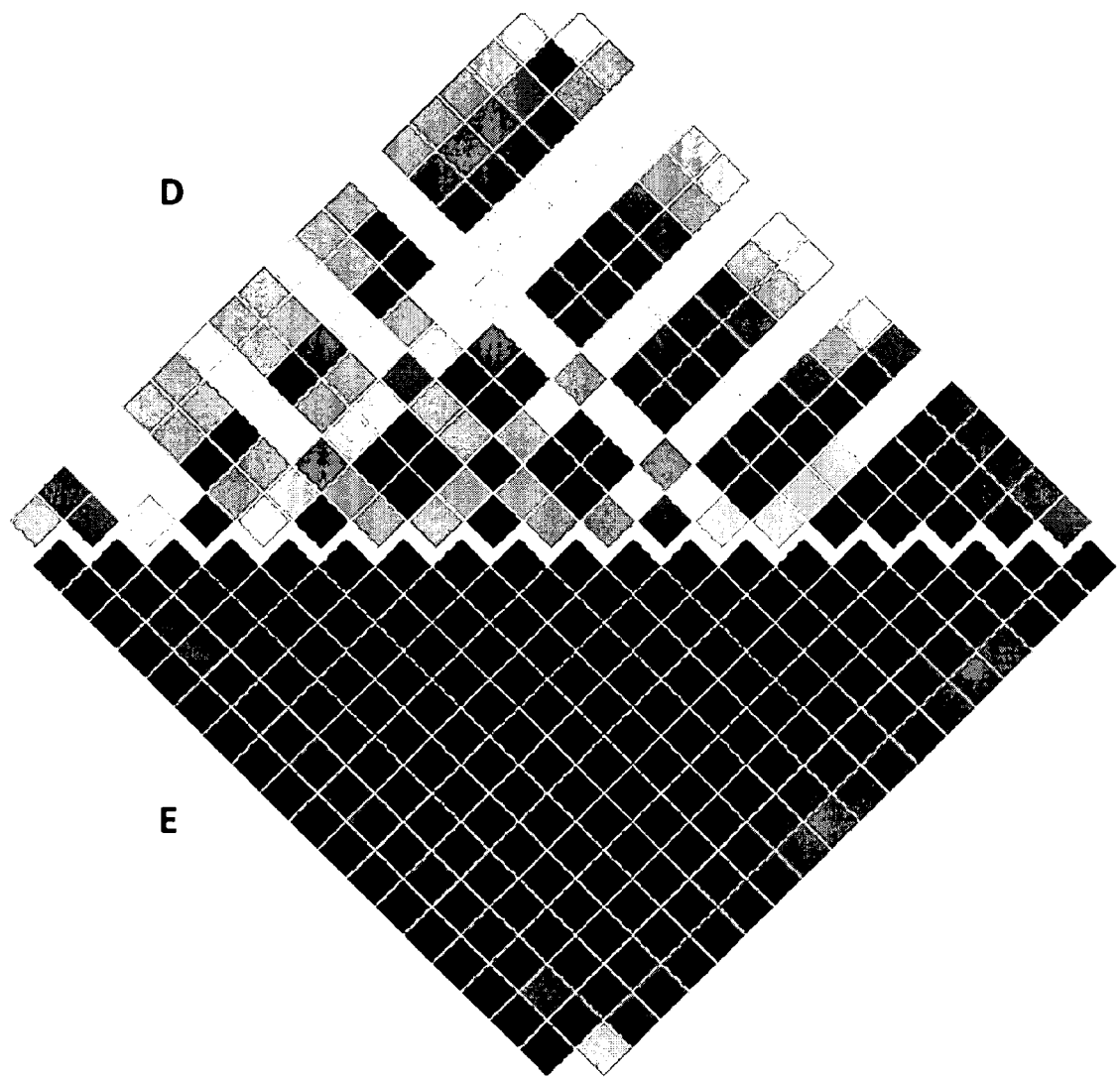

Asthma is a complex disease with both genetic and environmental components. However, the genetic susceptibility factors underpinning what is the most common chronic childhood disease remain largely unknown. We have carried out a whole genome association study genotyping over 545,000 SNPs in 569 North American asthmatics of European ancestry and 2136 disease-free controls. We describe a locus on chromosome 1q31 containing multiple common variants that are highly and reproducibly associated with pediatric onset asthma ($p<10^{-8}$). Upon replication, the chromosome 1q31 locus showed significant association with asthma in two independent cohorts comprising 2011 Northern European subjects ($p<10^{-7}$) and 3429 African American children ($p<10^{-4}$), respectively. Further analysis of the associated interval indicated that all the associated SNPs mapped to a block of high linkage disequilibrium (LD) that spanned the DENND1B gene and the 3' end of the CRB1 gene. DENND1B, a dendritic cell expressed protein, is a member of the DENN/MADD domain containing proteins that are known to interact with the TNFα receptor, a well established asthma pathway candidate.

In accordance with the present invention, high density SNP-based genotyping technology has been applied in GWA studies which have resulted in the identification of genes and genetic variants that contribute to asthma in well-defined pediatric study populations. This discovery impacts on millions of children in the US and the rest of the world with asthma.

Definitions:

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"Asthma-associated SNP or specific marker" is a SNP or marker which is associated with an increased or decreased risk of developing asthma not found normal patients who do not have this disease. Such markers may include but are not limited to nucleic acids, proteins encoded thereby, or other small molecules.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with asthma. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any asthma specific marker nucleic acid, but does not hybridize to other nucleotides. Also polynucleotide which "specifically hybridizes" may hybridize only to an airway specific marker, such as an asthma-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° \text{ C.} + 16.6 \text{ Log[Na+]} + 0.41(\% \text{ G+C}) - 0.63 (\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting DENN/D1B mRNA, for example, may be between 15-35 nucleotides in length, and more typically about 21 nucleotides in length. Exemplary siRNA sequences effective for down-modulating expression of the DENND1B are provided in Table 13.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, micro-injection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the asthma specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the asthma specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an asthma specific marker molecule, such as a marker shown in the tables provided below. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

Methods of Using Asthma-Associated SNPs for Diagnosing a Propensity for the Development of Asthma Asthma-related-SNP containing nucleic acids, including but not limited to those listed in the Tables provided below may be used for a variety of purposes in accordance with the present invention. Asthma-associated SNP containing DNA, RNA, or fragments thereof may be used as probes to detect the presence of and/or expression of asthma specific markers. Methods in which asthma specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting asthma-associated SNPs or the proteins encoded thereby may be conducted on any type of biological sample, including but not limited to body fluids (including blood, urine, serum, gastric lavage), any type of cell (such as brain cells, white blood cells, mononuclear cells) or body tissue.

From the foregoing discussion, it can be seen that asthma-associated SNP containing nucleic acids, vectors expressing the same, asthma SNP containing marker proteins and anti-asthma specific marker antibodies of the invention can be used to detect asthma associated SNPs in body tissue, cells, or fluid, and alter asthma SNP containing marker protein expression for purposes of assessing the genetic and protein interactions involved in the development of asthma.

In most embodiments for screening for asthma-associated SNPs, the asthma-associated SNP containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify asthma-associated SNP marker expression and accordingly, diagnose asthma.

Kits and Articles of Manufacture

Any of the aforementioned products can be incorporated into a kit which may contain a asthma-associated SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using Asthma-Associated SNPs for Development of Therapeutic Agents Since the SNPs identified herein have been associated with the etiology of asthma, methods for identifying agents that modulate the activity of the genes and their encoded products containing such SNPs should result in the generation of efficacious therapeutic agents for the treatment of this condition.

Chromosome 1 contains protein coding regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNP containing nucleic acids based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd.(Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as airway smooth muscle cells) which have a nonfunctional or altered asthma associated gene. These host cell lines or cells are defective at the polypeptide level. The host cell lines or cells are grown in the presence of drug compound. The rate of constriction or relaxation of the host cells is measured to determine if the compound is capable of regulating the airway responsiveness in the defective cells. Host cells contemplated for use in the present invention include but are not limited to bacterial cells, fungal cells, insect cells, mammalian cells, and plant cells. The asthma-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in Saccharomyces are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); *Picchia* vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, *Picchia* promoters such as the alcohol oxidase promoter, and *Saccharomyces* promoters such as the gal4 inducible promoter and the PGK constitutive promoter. In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the asthma-associated SNPs of the present invention or functional fragments thereof provide a system in which to screen potential compounds or agents for the ability to modulate the development of asthma. Thus, in one embodiment, the nucleic acid molecules of the invention may be used to create recombinant cell lines for use in assays to identify agents which modulate aspects of aberrant cytokine signaling associated with asthma and aberrant bronchoconstriction. Also provided herein are methods to screen for compounds capable of modulating the function of proteins encoded by SNP containing nucleic acids.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of asthma-associated SNP containing nucleic acids enables the production of strains of laboratory mice carrying the asthma-associated SNPs of the invention. Transgenic mice expressing the asthma-associated SNP of the invention provide a model system in which to examine the role of the protein encoded by the SNP containing nucleic acid in the development and progression towards asthma. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various processes associated with the asthmatic phenotype, including: aberrant bronchoconstriction, airway inflammation and altered IgE production. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of asthma-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated asthma-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing asthma-associated SNP containing nucleic acid as a targeted insertional cassette provides means to detect a successful insertion as visualized, for example, by acquisition of immunoreactivity to an antibody immunologically specific for the polypeptide encoded by asthma-associated SNP nucleic acid and, therefore, facilitates screening/selection of ES cells with the desired genotype.

As used herein, a knock-in animal is one in which the endogenous murine gene, for example, has been replaced with human asthma-associated SNP containing gene of the invention. Such knock-in animals provide an ideal model system for studying the development of asthma.

As used herein, the expression of a asthma-associated SNP containing nucleic acid, fragment thereof, or an asthma-associated SNP fusion protein can be targeted in a "tissue specific manner" or "cell type specific manner" using a vector in which nucleic acid sequences encoding all or a portion of asthma-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the asthma-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; and a CMV promoter for the expression of transgenes in airway smooth muscle cells.

Methods of use for the transgenic mice of the invention are also provided herein. Transgenic mice into which a nucleic acid containing the asthma-associated SNP or its encoded protein have been introduced are useful, for example, to develop screening methods to screen therapeutic agents to identify those capable of modulating the development of asthma.

Pharmaceuticals and Methods of Treatment

The elucidation of the role played by the asthma associated SNPs described herein in modulating the asthmatic phenotype facilitates the development of pharmaceutical compositions useful for treatment and diagnosis of asthma. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, aerosolized, intramuscular, and intraperitoneal routes.

The invention includes a method of treating asthma in a mammal. An exemplary method entails administering to the mammal a pharmaceutically effective amount of DENND1B siRNA. See Table 13. The siRNA inhibits the expression of DENND1B. Preferably, the mammal is a human. The term "patient" as used herein refers to a human.

Specific siRNA preparations directed at inhibiting the expression of DENND1B, as well as delivery methods are provided as a novel therapy to treat asthma. SiRNA oligonucleotides directed to DENND1B specifically hybridize with nucleic acids encoding DENND1B and interfere with DENND1B gene expression. The siRNA can be delivered to a patient in vivo either systemically or locally with carriers, as discussed below. The compositions of the invention may be used alone or in combination with other agents or genes encoding proteins to augment the efficacy of the compositions.

A "membrane permeant peptide sequence" refers to a peptide sequence which is able to facilitate penetration and entry of the DENND1B inhibitor across the cell membrane. Exemplary peptides include with out limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention siRNAs are delivered for therapeutic benefit. There are several ways to administer the siRNA of the invention to in vivo to treat asthma including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the siRNA to a patient will also vary depending on several factors including, but not limited to, the type and severity of the asthma to be treated, the route of administration, the age and overall health of the individual, the nature of the siRNA, and the like. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v35:p44 (2007).

Methods of the invention directed to treating asthma involve the administration of DENND1B siRNA in a pharmaceutical composition. DENND1B siRNA is administered to an individual as a pharmaceutical composition comprising DENND1B siRNA and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the DENND1B siRNA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the DENND1B siRNA.

One skilled in the art appreciates that a pharmaceutical composition comprising DENND1B siRNA can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising DENND1B siRNA inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

The pharmaceutical preparation comprises a siRNA targeting DENND1B or an expression vector encoding for an siRNA targeting DENND1B. Such pharmaceutical preparations can be administered to a patient for treating asthma.

Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

A formulated siRNA composition can be a composition comprising one or more siRNA molecules or a vector encoding one or more siRNA molecules independently or in combination with a cationic lipid, a neutral lipid, and/or a polyethyleneglycol-diacylglycerol (PEG-DAG) or PEG-cholesterol (PEG-Chol) conjugate. Non-limiting examples of expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500-505.

A lipid nanoparticle composition is a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. In one embodiment, the biologically active molecule is encapsulated in the lipid nanoparticle as a result of the process of providing and aqueous solution comprising a biologically active molecule of the invention (i.e., siRNA), providing an organic solution comprising lipid nanoparticle, mixing the two solutions, incubating the solutions, dilution, ultrafiltration, resulting in concentrations suitable to produce nanoparticle compositions.

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral siRNA delivery which can form complexes with negatively charged siRNA. The self-assembly PEG-ylated polycation polyethylenimine (PEI) has also been used to condense and protect siRNAs (Schiffelers et al., 2004, Nuc. Acids Res. 32: 141-110). The siRNA complex can be condensed into a nanoparticle to allow efficient uptake of the siRNA through endocytosis. Also, the nucleic acid-condensing property of protamine has been combined with specific antibodies to deliver siRNAs and can be used in the invention (Song et al., 2005, Nat Biotech. 23:709-717).

In order to treat an individual having asthma to alleviate a sign or symptom of the disease, DENND1B siRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of DENND1B siRNA required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having asthma.

The effective dose of DENND1B siRNA will depend on the mode of administration, and the weight of the individual being treated. The dosages described herein are generally those for an average adult but can be adjusted for the treatment of children. The dose will generally range from about 0.001 mg to about 1000 mg.

The concentration of DENND1B siRNA in a particular formulation will depend on the mode and frequency of administration. A given daily dosage can be administered in a single dose or in multiple doses so long as the DENND1B siRNA concentration in the formulation results in the desired daily dosage. One skilled in the art can adjust the amount of DENND1B siRNA in the formulation to allow administration of a single dose or in multiple doses that provide the desired concentration of DENND1B siRNA over a given period of time.

In an individual suffering from asthma, in particular a more severe form of the disease, administration of DENND1B siRNA can be particularly useful when administered in combination, for example, with a conventional agent for treating such a disease. The skilled artisan would administer DENND1B siRNA, alone or in combination and would monitor the effectiveness of such treatment using routine methods such as pulmonary function determination, radiologic, immunologic or, where indicated, histopathologic methods. Other conventional agents for the treatment of asthma include steroid or administration of other agents that alleviate the symptoms underlying the disease.

Administration of the pharmaceutical preparation is preferably in an "effective amount" this being sufficient to show benefit to the individual. This amount prevents, alleviates, abates, or otherwise reduces the severity of asthma symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

The following example is provided to illustrate certain embodiments of the invention. It is not intended to limit the invention in any way.

EXAMPLE I

Identification of Asthma Associated SNPs in a Pediatric Population

We carried out a genome wide association study in a cohort of pediatric asthma patients and matched controls consisting of 793 North American cases of European ancestry (EA) with persistent asthma requiring daily inhaled glucocorticoids for symptom control, and 1988 matched control subjects without asthma. The association results were replicated in an independent set of 917 EA asthma cases and 1546 matched controls. We also analyzed and report on 1667 children of African-American (AA) ancestry with physician diagnosed asthma and 2045 AA controls.

In addition to replicating the previously reported ORMDL3 locus on 17q21 in our meta-analysis, eight SNPs at 1q31 reached genome-wide significance in the Caucasian discovery cohort, top SNP rs2786098 (P=8.5×10$^{-9}$, OR=0.63) and replicated in the independent EA cohort (combined P=9.3×10$^{-11}$, OR=0.70). The same SNPs were also strongly associated with asthma in the AA children (combined P across all samples 1.6×10$^{-13}$), albeit with the alternate allele due to allele tagging differences and heterogeneity in the local patterns of linkage disequilibrium between these populations. The associated interval contains DENND1B, a gene expressed by natural killer cells and dendritic cells that encodes a protein predicted to interact with the TNFα receptor, whose family members are known to regulate neurotransmitter release and exocytosis in neuronal cells.

The following material and methods are provided to facilitate the practice of Example I.

This study was approved by the institutional review board of the Children's Hospital of Philadelphia (CHOP). Parental informed consent was obtained from all participants in this study for the purpose of DNA collection and genotyping.

Study Subjects

The asthma discovery cohort consisted of 793 patients of European ancestry (EA) recruited at CHOP. The mean age of these cases was 7.4±4.5 SD years and 53% were males. All the subjects had persistent asthma necessitating regular administration of glucocorticoid medications for symptom control. Disease severity matched steps 2-6 as reported in the Asthma Expert Panel-3 guidelines[11].

The combined EA replication cohort consisted of 917 patients with physician-diagnosed asthma who were recruited from three different study sites: 1) 343 unrelated patients (parents and children) from the Copenhagen Prospective Study on Asthma in Childhood (COPSAC) in Denmark with asthma diagnosed during childhood[12,13]; 2) 410 unrelated children from the German MAGIC cohort with history of recurrent asthma exacerbations and hospitalizations[6] and; 3) 164 unrelated children from the British MRCA cohort diagnosed with severe asthma[6] (Table 1). COPSAC is a single-center birth cohort study of children of asthmatic mothers. We genotyped 304 mothers all of whom had physician diagnosed asthma by the age of 7 years; 35 fathers with physician-diagnosed asthma during childhood; and 4 children diagnosed with moderate to severe asthma at the age of 6 years. These children were unrelated to the parents used in the study. The COPSAC patients have been extensively phenotyped as described previously[12,13]. The German MAGIC subjects included in this study matched closely the phenotypic severity level and demographic profile of the discovery cohort. The British MRCA cohort consist of multiplex families with severe asthma; only one individual per family was used in this study. Population details and genotyping procedures for the MRCA and MAGIC cohorts have been previously reported[6].

The African American (AA) cohort consisted of 1667 cases with physician diagnosed asthma, 1223 of whom were recruited at CHOP and 444 at Johns Hopkins and Howard University. The mean age of these cases was 7.4±SD 5.7 years and 57% were males.

The control groups used in the discovery phase included 1988 self-reported Caucasian children of European ancestry who were recruited at CHOP (mean age was 8.5±5.6 SD years and 50% male). The replication control group included 210 Danish samples with no history of asthma collected as part of the COPSAC study and 1336 British samples genotyped by the Wellcome Trust Case Control Consortium (www.b58cgene.sgul.ac.uk). The African American controls consisted of 2045 children of self-reported AA ancestry 1652 of whom were recruited at CHOP and 393 at Johns Hopkins (mean age was 6.6±7.7 SD years and 49% were males). CHOP patients and controls were recruited by CHOP clinicians and nursing staff within the CHOP Health Care Network, including four primary care clinics and several group practices and outpatient practices that included well child visits. All CHOP controls screened negative for asthma or reactive airway diseases based on questionnaire information (Table 1).

For a secondary analysis of age of onset, we surveyed the electronic medical records database at CHOP taking the date of first asthma diagnosis or first prescription of asthma-specific medication as the approximate date of asthma onset. A total of 793 EA cases and 2109 AA cases ranging in age from 2 to 19 years were included in the analysis.

To reduce the risk of population stratification due to inaccurate self-reported ancestry all internal patients and controls were initially screened using the STRUCTURE package[14], we used 220 ancestry informative markers (AIMs) and spiked the test sample set with 90 CEPH, Yoruban and Chinese/Japanese individuals genotyped as part of the HapMap project to improve clustering. Samples were excluded from the EA set if their inferred proportion of ancestry was less than 90% that of the CEU cluster and from the AA set if it was less than 70% of the Yoruban cluster. All Asian samples were excluded from the analysis.

To minimize confounding due to population stratification, each set of cases was matched to its respective set of controls by 'genetic matching' as previously described[15]. 'Genetic matching' is a principal component analysis (PCA) based method of matching cases with controls that minimizes the effects of population stratification in GWA studies. We computed principal components for our dataset by running smart pca, a part of the EIGENSTRAT package, on 100,000 random autosomal SNPs and applied a matching algorithm implemented in MATLAB to the output. The matching algorithm assigns each sample a coordinate based on k eigen value-scaled principal components. It then matches each case to m unique controls within a distance d, keeping only cases that match exactly m controls. The distance thresholds were manually optimized for each data set to minimize GIF and maximize power (i.e. number of cases). In this study, we matched the CHOP discovery cases to 3 controls, using 3 principal components and a distance threshold of 0.07. African American cases were matched to 2 controls at a distance threshold of 0.05 and the replication cohort cases were matched to 2 controls at a distance threshold of 0.04.

Genotyping

All CHOP and COPSAC samples were genotyped on the Illumina HH550 BeadChip. The Johns Hopkins and Howard University AA samples were genotyped on the Illumina 650Y Bead Chip. The MRCA, MAGIC and ISAAC samples were genotyped on HH300 Bead Chip as previously described[6]. The 1958 birth cohort samples were genotyped on the HH550 Bead Chip by the Wellcome Trust Case Control Consortium (WTCCC)[4].

We performed high throughput genome-wide SNP genotyping, using the Illumina Infinium™ II HumanHap550 BeadChip technology[16,17] (Illumina, San Diego) at the Center for Applied Genomics at CHOP, as previously described[18]. Quality control values for the individual data sets are presented in Table 4.

Statistical Analysis

Statistical tests for association were carried out using the software package plink (http://pngu.mgh.harvard.edu/~purcell/plink/index.shtml) for genotyped SNPs and SNPTEST[19] when imputed SNPs were included in the analyses to take the genotype uncertainty introduced by the imputation into account, a call threshold of 0.9 was used, SNPs with an info score below 0.5 were excluded. Single marker analyses for the genome-wide data were carried out using the Cochran-Armitage trend. Combined P-values across the Caucasian data sets were obtained using both Fisher's method and fixed-effect meta-analyses as implemented in the R package "meta". To combine the Caucasian data set and the African American data set in a joint analysis, the logistic regression model was fitted to include an additional predictor variable for race by genotype interactions in view of the observed differences in directionality of effect between these two populations at this locus.

Imputation of untyped markers (~2M) was carried out using IMPUTE[19]. Reference phased CEU haplotypes and recombination rates were obtained from the HapMap project; Phase II build 22. Imputation was carried out in 1 Mb intervals using an effective population size of 11418 as recommended. Over 99% of genotypes would have been called with over 96% concordance across all runs at a call threshold of 0.5.

Conditional SNP regression analyses were carried out in plink, the allele dosages of the conditioning SNP were included as covariates in the logistic regression models. For the age of onset analysis, we performed an analysis of variance (ANOVA) with the general linear models procedure in R (www.r-project.org),Independent variables for each ANOVA were the log transformed age of onset and the individual SNP genotype with additive encoding.

Results

We performed a GWA study in 793 North American children of European ancestry with physician-diagnosed asthma necessitating daily corticosteroid administration for symptom control and 1988 disease-free controls. Cochran-Armitage trend test statistics were calculated at all markers following quality control filtering. In addition to self-reported ancestry, all cases and controls were initially screened at ancestry informative markers (AIMs) using the STRUCTURE software package to reduce the risk of population stratification due to misspecification of self-reported ancestry. Cases were subsequently 'genetically matched' to controls by principal component analysis as previously described[15].

Eight SNPs reached genome-wide significance following Bonferroni correction for multiple testing. All eight SNPs mapped to a 540 kb interval on 1q31.3 (top marker, rs2786098 MAFs 15.2% in cases and 22.2% in controls, OR=0.63, [95% CI 0.54-0.73], P=8.55×10$^{-9}$). The interval contained a further 12 markers in strong linkage disequilibrium (LD) ($r^2$>0.45) that also showed strong evidence of association (P-value range=2.1×10$^{-5}$-1.4×10$^{-7}$; OR range=0.62-0.67) (Table 2). All 20 associated SNPs map to asingle LD block that spans the DENND1B (DENN/MADD domain containing 1 B)gene as well as the 3' end of the CRB1 (drosophila crumbs homolog 1)gene (FIG. 1). Imputation of a further 2 M untyped SNPs genome-wide yielded an additional 102 SNPs in the chromosome 1q31 LD block that were significantly associated with asthma. Eight imputed markers were more significantly associated than rs2786098, the top performing genotyped SNP, (P-values range 7.05×10$^{-9}$-9.77×10$^{-5}$; OR range 0.62-0.78) (Table 6). No other imputed SNPs reached genome-wide significance.

We next sought to replicate the findings in an independent sample of pediatric asthma cases of European ancestry. We analyzed a combined cohort of 917 pediatric onset Northern European asthma patients from three different study sites and 1546 control samples (Table 1). There was no overlap between the patients or controls in the discovery and replication sets. Two of the replication sets were genotyped on the HH300K Bead Chips, the combined analysis was therefore carried out on approximately 317,000 SNPs that were common to the HH550 and HH300 Bead Chips and the missing SNPs imputed. All reported P-values were corrected for the genotype uncertainty that is introduced by the imputation. To reduce the effects of population stratification we 'genetically matched' cases to controls by principal component analysis as previously described[15].

Of the twenty associated SNPs in the discovery cohort, eighteen were significantly associated with asthma (P-value range=0.043-6.5×10$^{-4}$; OR range=0.69-0.89) (Tables 2 and 6). The most significantly associated SNP across both Caucasian cohorts following the combination of P-values by Fisher's method and a fixed effects meta-analysis remained rs2786098 (P-value=3.9×10$^{-11}$; OR 0.7 95% CI 0.63-0.78). Results of the individual replication sets are presented in Table 7.

Figure 2:
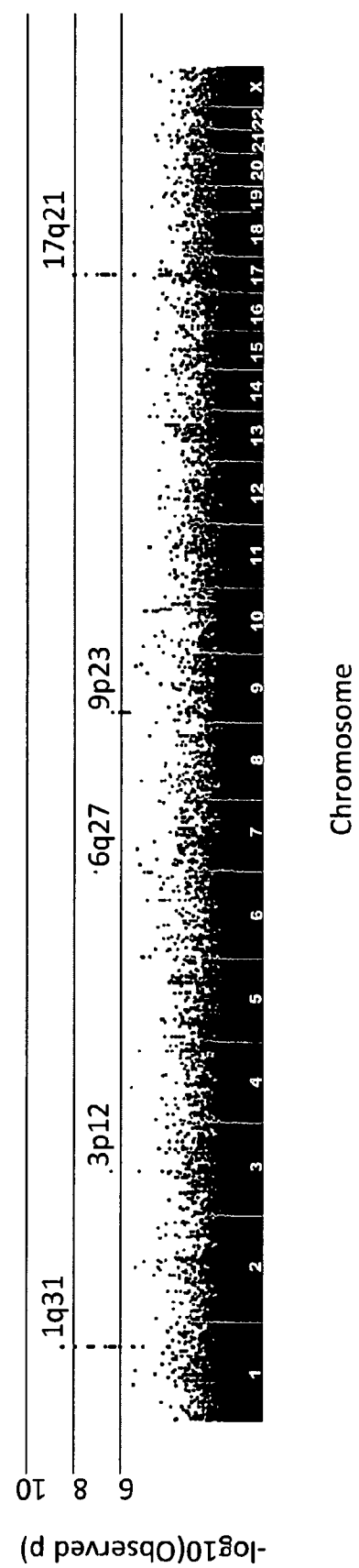
FIG. 2: Manhattan Plot of the combined European ancestry asthma cases. Log10 P-values are plotted against physical distance. Two loci at chromosome 1q31 and 17q21 were significantly associated with asthma following Bonferroni correction.

We subsequently carried out a combined analysis of all the European ancestry asthma cases and controls on the 2 million imputed and genotyped SNPs. Apart from the previously reported 17q21 locus and the 1q31 locus, one SNP at 6q27 surpassed the genome-wide threshold for significance. Two other loci at 3p12 and 9p23 showed a trend for association (FIG. 2, Table 10).

Figure 3:
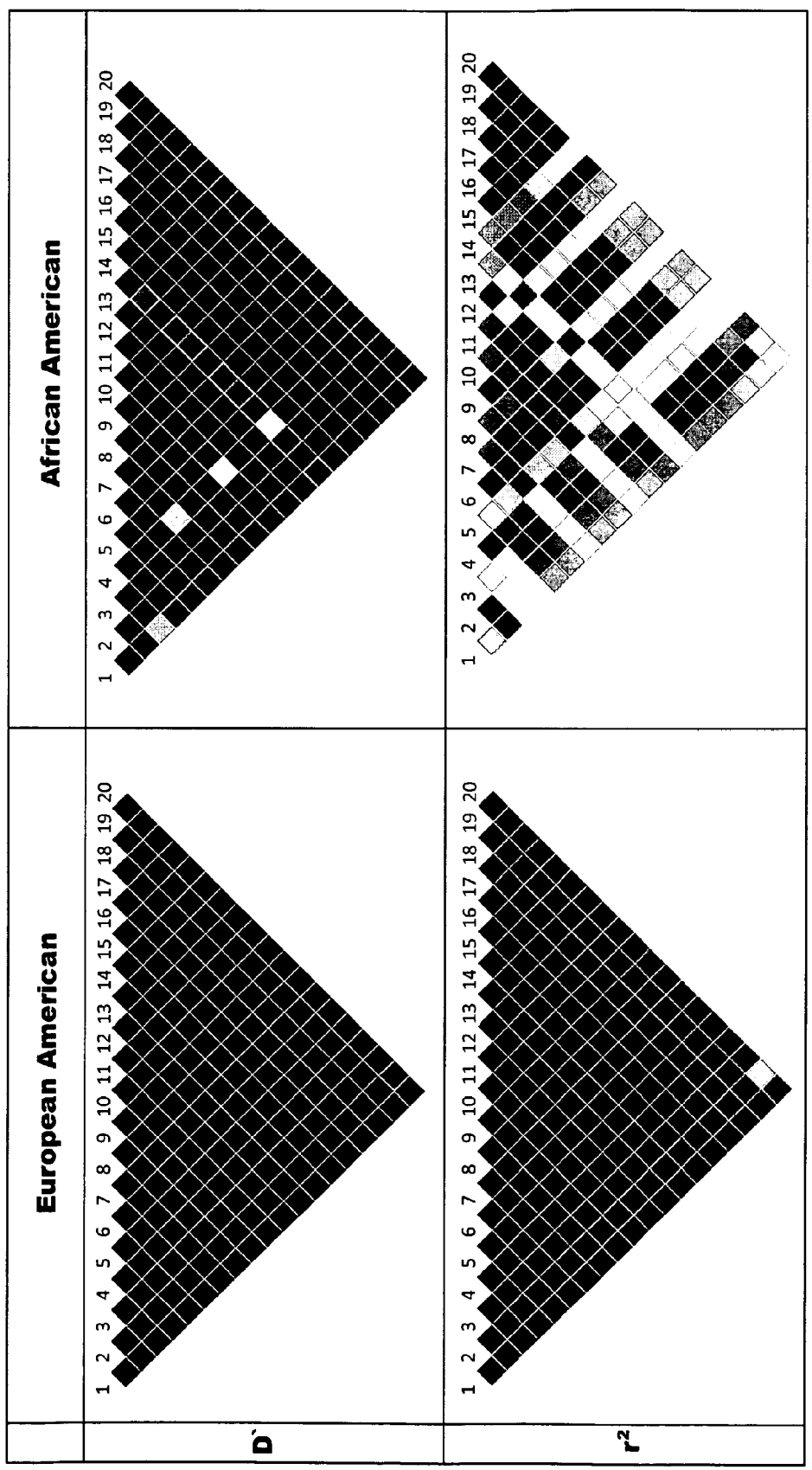
FIG. 3: D' and $r^2$ LD plots of the CHOP discovery EA and AA control samples. The numbered SNPs 1-20 correspond to the associated SNPs listed in table 2.

To determine if this locus also contributes to asthma in children of African ancestry, we tested the interval for association in a large pediatric cohort of 1667 AA subjects with physician-diagnosed asthma and 2045 disease-free controls. Seventeen of the twenty markers were significantly associated with asthma, albeit with the alternate allele (P-value range=0.01-4.2×10$^{-7}$; OR range=0.53-0.96) (Tables 2 and 11). Following the combination of P-values across all three samples sets using a joint test of the SNP effect and SNP race interaction, rs2786098 remained the most strongly associated (P-value=1.68×10$^{-13}$; Table 2). Plotting the r$^2$ within the associated interval in the AA CHOP control samples showed marked degradation in the LD structure compared to EA discovery control samples (FIGS. 1 and 3). The most significant association in the AA cohort was with a small block of LD formed by four SNPs in intron 2 of DENND1B (rs1747815, rs1775456, rs1924518 and rs1775444, P-value range=3.1×10$^{-7}$-9.4×10$^{-7}$; OR=0.53) (Table 2). However, the association extended over the same interval as the EA samples. We therefore sought to determine if there was more than one SNP with independent effects in the interval in the African American samples. We carried out logistic regression analyses in the EA and AA samples conditioning on the most significantly associated SNP in the Caucasians, rs2786098. The conditional analysis in the EA samples effectively nullified the association in the interval whereas ten SNPs remained significantly associated in the AA set, the most significant of which was rs1775456 (P-value 2.4×10$^{-4}$) (Table 3). Conditioning on rs1775456 nullified the association in both EA and AA samples suggesting that the associated variant is in the proximity of rs1775456.

Finally, to further investigate the observed association with asthma we analyzed the EA and AA cases for age of onset effects. In both EA and AA samples there was a significant difference in the distribution of genotypes assuming an additive model according to age of onset, 9 SNPs were significant following ANOVA in the EAs and 3 in the AAs (Table 12). In the EAs the protective minor allele homozygotes were more frequent in the patients with later ages of onset, whereas in the African Americans the effect was reversed with an increased frequency of the risk ancestral homozyotes in the younger onset cases.

Discussion

We have identified and replicated a genome-wide significant locus at 1q31 in asthma patients of Northern European ancestry and also observed association in an asthma cohort of African ancestry at this same locus. The association in the African Americans was observed with the opposite allele to that of the EA samples. Our investigations into the observed risk allele reversal in the African Americans suggest that at least one of the tagged causal variants may have arisen independently. Allele reversal at a shared causal variant can be attributed to the considerable differences in the underlying genomic architectures at this locus between individuals of African and European ancestry, as previously demonstrated[20].

Two genes map to this locus CRB1 and DENND1B. Functionally, CRB1 encodes a transmembrane protein involved in the morphogenesis and maintenance of the retina epithelia[21]. CRB1 mutations have been shown to result in retinitis pigmentosa (RP12)[22]. Expression of the full length gene and its splice forms is restricted to the retina and brain[22,23]. As such it is an unlikely asthma candidate gene.

In contrast to CRB1, the DENND1B gene remains poorly characterized. It encodes a DENN/MADD (differentially expressed in normal versus neoplastic/mitogen-activated protein kinase-activating death) domain first identified as a tumor necrosis factor (TNF) α receptor type 1 (TNFR1) binding protein[24]. DENN/MADD is a part of a signaling protein complex that is localized to the cytosol and exerts multiple functions by using different binding partners including TNFR1. DENN/MADD has been shown to act as a negative regulator of TNFR1 signaling in response to cytokine-promoted stress[24], regulate recycling of small G proteins and play an essential role in Ca$^{2+}$-dependent neurotransmitter release and exocytosis[25].

Figure 4:
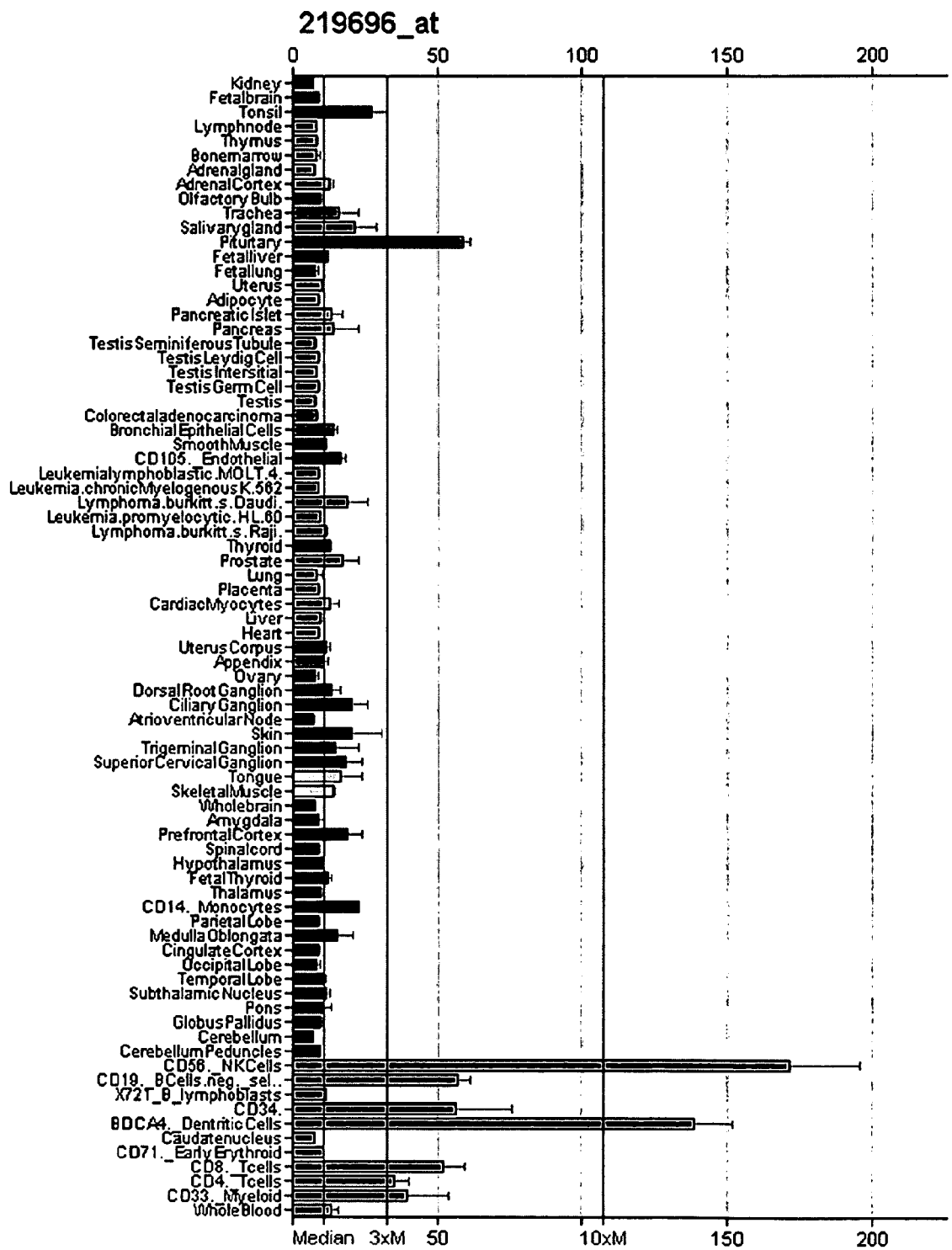
FIG. 4: Median DENND1B expression across all tissues. The purple lines correspond to 3 times the median value (3×M) and 10 times the median (10×M). Dendritic cells and Natural Killer cells (light blue columns) express DENND1B over 10 times the median value.

DENND1B is expressed in a subset of dendritic cells (DCs), BDCA3$^+$DCs[26] and BDCA4$^+$DCs and natural killer (NK) cells (FIG. 4)[27]. DCs are a distinct lineage of leukocytes that function as the gate-keepers of innate and adaptive immune responses, by modulating tolerance or triggering immunity through the release and regulation of various cytokines[28]. Immunological memory is also a fundamental feature of the adaptive immune system and DENND1B is significantly upregulated in effector memory T cells compared to naïve T cells [29] suggesting a role for DENND1B in the immune response to previously encountered pathogens.

The cardinal features of asthma, airway inflammation and airway hyperresponsiveness, both of which are associated with atopy and elevated IgE levels, have been postulated to arise from an aberrant T cell response to viral or bacterial infection or to common allergens[12]. T cells are activated through exposure to antigens on dendritic cell surfaces; in asthma a larger proportion of activated T cells develop a $T_H2$ pattern that results in the expression of T cell survival cytokines such as IL-5 and IL-13[30]. DENND1B, which is expressed on both DCs and activated T cells, functions to downregulate TNFR1 signaling thereby modulating the $T_H1$-$T_H2$ cytokine cascade and other inflammatory signaling pathways.

In conclusion, we have identified a locus on chromosome 1q31 that is significantly associated with moderate to severe persistent asthma at the genome-wide level and replicates in independent cohorts of asthma patients of different ethnic backgrounds, including African Americans and Caucasians of Northern European ancestry. Age of onset analysis indicates the variants predispose to early onset asthma. The observed association in AA children places this locus amongst a select few asthma genes, IL4, IL13, CD14, ADRB2, FcER1B, AL4RA and most recently ORMDL3 (the only one detected through GWA so far), that have been found to predispose to asthma in multiple populations[6, 31, 32], including our own.[33] Of the two genes in the associated interval, the DENND1B gene product has a putative role in the adaptive immune system. As such the characterization of the role of DENND1B in asthma together with other gene products in this network could lead to a better understanding of the underlying disease etiology.

TABLE 1

Composition of the Discovery and Replication cohorts and the Illumina Bead Chip on which they were genotyped.

|  | Caucasian discovery cohort | African American cohort | | | Caucasian Replication set | | | | |
|---|---|---|---|---|---|---|---|---|---|
|  | CHOP | CHOP | JH | Total | COPSAC | MAGIC/ISAAC | MRCA | WTCCC | Total |
| Asthmatic | 793 | 1223 | 444 | 1667 | 343 | 410 | 164 | NA | 917 |
| Controls | 1988 | 1652 | 393 | 2045 | 210 | NA | NA | 1336 | 1546 |
| Illumina BeadChip | HH550K | HH550K | HH650YK | — | HH550K | HH300K | HH300K | HH550K | — |

TABLE 2

Associated SNP P-values and odds ratios in the CHOP EA discovery cohort, the combined replication set and the African American (AA) samples.

| | | | CHOP discovery | | | EA replication | | Combined Caucasian | | | AA | | Combined All |
|---|---|---|---|---|---|---|---|---|---|---|---|---|---|
| SNP | Pos | A1 | Freq | OR | P | OR | P | OR | P | A2 | OR | P | P |
| *rs2786098 | 194057565 | A | 0.152 | 0.63 | $8.55 \times 10^{-9}$ | 0.77 | $6.47 \times 10^{-4}$ | 0.70 | $9.33 \times 10^{-11}$ | C | 0.71 | $3.77 \times 10^{-5}$ | $1.68 \times 10^{-13}$ |
| rs2821106 | 194115942 | A | 0.0927 | 0.66 | $2.06 \times 10^{-5}$ | 0.81 | $1.81 \times 10^{-3}$ | 0.73 | $6.32 \times 10^{-06}$ | G | 0.49 | $3.52 \times 10^{-5}$ | $2.01 \times 10^{-9}$ |
| *rs12134409 | 194123724 | T | 0.153 | 0.64 | $2.72 \times 10^{-8}$ | 0.77 | $5.37 \times 10^{-4}$ | 0.71 | $1.64 \times 10^{-10}$ | C | 0.66 | $3.80 \times 10^{-5}$ | $7.30 \times 10^{-13}$ |
| rs2111931 | 194260875 | C | 0.147 | 0.65 | $8.71 \times 10^{-8}$ | 0.69 | $3.21 \times 10^{-3}$ | 0.66 | $4.58 \times 10^{-9}$ | T | 0.85 | $3.32 \times 10^{-3}$ | $6.08 \times 10^{-10}$ |
| rs10737692 | 194280590 | A | 0.148 | 0.65 | $1.40 \times 10^{-7}$ | 0.69 | $3.47 \times 10^{-3}$ | 0.66 | $6.95 \times 10^{-9}$ | G | 0.88 | 0.017 | $3.51 \times 10^{-9}$ |
| rs12127378 | 194332749 | C | 0.155 | 0.66 | $2.84 \times 10^{-7}$ | 0.70 | $5.84 \times 10^{-3}$ | 0.67 | $1.83 \times 10^{-8}$ | T | 0.73 | $4.78 \times 10^{-4}$ | $4.38 \times 10^{-10}$ |
| rs12041661 | 194333325 | A | 0.155 | 0.67 | $3.50 \times 10^{-7}$ | 0.70 | $6.18 \times 10^{-3}$ | 0.68 | $2.43 \times 10^{-8}$ | C | 0.72 | $2.81 \times 10^{-4}$ | $3.50 \times 10^{-10}$ |
| rs10442656 | 194338365 | T | 0.156 | 0.67 | $3.58 \times 10^{-7}$ | 0.82 | $6.16 \times 10^{-3}$ | 0.74 | $4.69 \times 10^{-8}$ | C | 0.96 | 0.429 | $1.66 \times 10^{-7}$ |
| rs2477070 | 194344416 | G | 0.154 | 0.66 | $1.89 \times 10^{-7}$ | 0.82 | $6.18 \times 10^{-3}$ | 0.74 | $2.96 \times 10^{-8}$ | A | 0.74 | $8.00 \times 10^{-4}$ | $5.56 \times 10^{-10}$ |
| rs1747827 | 194347048 | T | 0.155 | 0.67 | $3.60 \times 10^{-7}$ | 0.81 | $5.87 \times 10^{-3}$ | 0.74 | $4.45 \times 10^{-8}$ | C | 0.73 | $5.09 \times 10^{-4}$ | $5.93 \times 10^{-10}$ |
| rs2488411 | 194390456 | C | 0.154 | 0.66 | $1.48 \times 10^{-7}$ | 0.70 | $6.04 \times 10^{-3}$ | 0.67 | $1.05 \times 10^{-8}$ | T | 0.95 | 0.398 | $9.34 \times 10^{-8}$ |
| rs1891497 | 194391212 | A | 0.154 | 0.66 | $2.03 \times 10^{-7}$ | 0.70 | $6.39 \times 10^{-3}$ | 0.67 | $1.41 \times 10^{-8}$ | G | 0.76 | $1.62 \times 10^{-3}$ | $1.19 \times 10^{-9}$ |
| rs1747815 | 194429760 | A | 0.15 | 0.65 | $8.05 \times 10^{-8}$ | 0.83 | 0.017 | 0.74 | $5.45 \times 10^{-8}$ | G | 0.53 | $3.14 \times 10^{-7}$ | $5.04 \times 10^{-13}$ |
| rs1775454 | 194458955 | T | 0.146 | 0.65 | $1.96 \times 10^{-7}$ | 0.90 | 0.057 | 0.77 | $4.15 \times 10^{-6}$ | C | 0.90 | 0.119 | $1.77 \times 10^{-6}$ |
| rs1775456 | 194464712 | G | 0.147 | 0.65 | $8.45 \times 10^{-8}$ | 0.86 | 0.043 | 0.75 | $2.95 \times 10^{-7}$ | A | 0.53 | $4.27 \times 10^{-7}$ | $3.71 \times 10^{-12}$ |
| rs1924518 | 194469984 | A | 0.149 | 0.65 | $5.81 \times 10^{-8}$ | 0.73 | 0.071 | 0.66 | $1.08 \times 10^{-8}$ | G | 0.53 | $8.61 \times 10^{-7}$ | $2.82 \times 10^{-9}$ |
| rs1775444 | 194472347 | T | 0.149 | 0.65 | $5.81 \times 10^{-8}$ | 0.86 | 0.043 | 0.75 | $2.47 \times 10^{-7}$ | C | 0.53 | $9.43 \times 10^{-7}$ | $5.53 \times 10^{-12}$ |
| rs12026183 | 194544689 | T | 0.131 | 0.62 | $1.06 \times 10^{-8}$ | 0.86 | 0.025 | 0.73 | $1.31 \times 10^{-7}$ | C | 0.55 | $3.99 \times 10^{-6}$ | $5.45 \times 10^{-12}$ |
| rs10922300 | 194546342 | T | 0.12 | 0.65 | $1.01 \times 10^{-6}$ | 0.79 | $3.16 \times 10^{-3}$ | 0.71 | $8.11 \times 10^{-8}$ | C | 0.59 | $2.36 \times 10^{-4}$ | $7.44 \times 10^{-11}$ |
| rs10922326 | 194599319 | G | 0.117 | 0.67 | $9.81 \times 10^{-6}$ | 0.70 | $8.32 \times 10^{-3}$ | 0.68 | $1.30 \times 10^{-6}$ | T | 0.62 | $3.20 \times 10^{-5}$ | $1.97 \times 10^{-9}$ |

Freq: Minor allele frequencies in the CHOP discovery cases. A1: protective allele in Caucasians; A2 risk allele in AAs. Combined P-values from fixed-effect meta-analyses.
*rs2786098 and rs12134409 imputed in the MAGIC and MRCA cohorts.
When all samples were combined, P-values were obtained by jointly testing the SNP and SNP by race interaction effects.

TABLES 3A and 3B

Logistic regression at the 1q31 locus in the EA discovery and AA cohorts after conditioning on A) rs2786098 and B) rs1775456.

Table 3A

Conditioning on rs2786098

| SNP | Position | EA P-val | AA P-val |
|---|---|---|---|
| rs2821106 | 194115942 | 0.521 | 0.013 |
| rs12134409 | 194123724 | 0.109 | 0.044 |
| rs2111931 | 194260875 | 0.101 | 0.021 |
| rs10737692 | 194280590 | 0.076 | 0.183 |
| rs12127378 | 194332749 | 0.445 | 0.056 |
| rs12041661 | 194333325 | 0.475 | 0.057 |
| rs10442656 | 194338365 | 0.507 | 0.430 |
| rs2477070 | 194344416 | 0.446 | 0.089 |
| rs1747827 | 194347048 | 0.482 | 0.078 |
| rs2488411 | 194390456 | 0.310 | 0.485 |
| rs1891497 | 194391212 | 0.359 | 0.157 |
| rs1747815 | 194429760 | 0.115 | $5.00 \times 10^{-4}$ |
| rs1775454 | 194458955 | 0.250 | 0.671 |
| rs1775456 | 194464712 | 0.094 | $2.44 \times 10^{-4}$ |
| rs1924518 | 194469984 | 0.124 | $6.04 \times 10^{-4}$ |
| rs1775444 | 194472347 | 0.124 | $8.59 \times 10^{-4}$ |
| rs12026183 | 194544689 | 0.034 | $3.05 \times 10^{-3}$ |
| rs10922300 | 194546342 | 0.180 | 0.019 |
| rs10922326 | 194599319 | 0.166 | $2.26 \times 10^{-3}$ |

Table 3B

Conditioning on rs1775456

| SNP | Position | EA P-val | AA P-val |
|---|---|---|---|
| rs2786098 | 194057565 | 0.195 | 0.077 |
| rs2821106 | 194115942 | 0.722 | 0.443 |
| rs12134409 | 194123724 | 0.158 | 0.872 |
| rs2111931 | 194260875 | 0.225 | 0.236 |
| rs10737692 | 194280590 | 0.157 | 0.347 |
| rs12127378 | 194332749 | 0.752 | 0.945 |
| rs12041661 | 194333325 | 0.677 | 0.868 |
| rs10442656 | 194338365 | 0.689 | 0.279 |
| rs2477070 | 194344416 | 0.746 | 0.661 |
| rs1747827 | 194347048 | 0.674 | 0.708 |
| rs2488411 | 194390456 | 0.943 | 0.301 |
| rs1891497 | 194391212 | 0.887 | 0.428 |

TABLES 3A and 3B-continued

Logistic regression at the 1q31 locus in the EA discovery and AA cohorts after conditioning on A) rs2786098 and B) rs1775456.

| | | | |
|---|---|---|---|
| rs1747815 | 194429760 | 0.399 | 0.922 |
| rs1775454 | 194458955 | 0.679 | 0.710 |
| rs12026183 | 194544689 | 0.116 | 0.897 |
| rs10922300 | 194546342 | 0.290 | 0.539 |
| rs10922326 | 194599319 | 0.348 | 0.314 |

TABLE 4

Genotyping quality control values for the individual sample sets.

| Sample | Low Genotyping (<98%) Case | Low Genotyping (<98%) Control | SNP call rates < 95% | MAF < 1% | HWE P < $10^{-5}$ | GIF |
|---|---|---|---|---|---|---|
| Discovery | 42 | 132 | 8557 | 22087 | 2110 | 1.06 |
| COPSAC | 5 | 14 | 8508 | 24121 | 526 | 1.03 |
| MAGIC | 15 | 62 | 8357 | 1910 | 550 | 1.04 |
| MRCA | 11 | 56 | 7436 | 215 | 541 | 1.01 |
| AA | 14 | 43 | 8707 | 5645 | 4032 | 1.13 |

TABLE 5

Call rates and Hardy Weinberg P-values for the asthma associated SNPs in the discovery cohort.

| SNP | Percent Missing genotype | O(HET)-Control | E(HET)-Control | P-Control | O(HET)-All | E(HET)-All | P-All | O(HET)-Case | E(HET)-Case | P-Case |
|---|---|---|---|---|---|---|---|---|---|---|
| rs2786098 | 0.006 | 0.324 | 0.342 | 0.022 | 0.309 | 0.320 | 0.074 | 0.271 | 0.258 | 0.179 |
| rs2821106 | 0.002 | 0.223 | 0.229 | 0.185 | 0.212 | 0.213 | 0.795 | 0.184 | 0.169 | 0.006 |
| rs12134409 | 0.008 | 0.328 | 0.341 | 0.096 | 0.312 | 0.319 | 0.203 | 0.270 | 0.259 | 0.283 |
| rs2111931 | 0.003 | 0.323 | 0.329 | 0.323 | 0.307 | 0.309 | 0.766 | 0.269 | 0.252 | 0.054 |
| rs10737692 | 0.002 | 0.323 | 0.329 | 0.390 | 0.307 | 0.309 | 0.766 | 0.268 | 0.253 | 0.099 |
| rs12127378 | 0.010 | 0.330 | 0.337 | 0.363 | 0.316 | 0.317 | 0.815 | 0.279 | 0.262 | 0.064 |
| rs12041661 | 0.007 | 0.330 | 0.335 | 0.475 | 0.316 | 0.316 | 1 | 0.280 | 0.263 | 0.064 |
| rs10442656 | 0.002 | 0.333 | 0.338 | 0.479 | 0.318 | 0.319 | 0.954 | 0.282 | 0.264 | 0.065 |
| rs2477070 | 0.003 | 0.332 | 0.338 | 0.440 | 0.317 | 0.318 | 0.908 | 0.279 | 0.263 | 0.065 |
| rs1747827 | 0.008 | 0.331 | 0.337 | 0.476 | 0.317 | 0.317 | 1 | 0.281 | 0.264 | 0.065 |
| rs2488411 | 0.005 | 0.333 | 0.338 | 0.441 | 0.318 | 0.318 | 0.908 | 0.279 | 0.262 | 0.065 |
| rs1891497 | 0.013 | 0.330 | 0.336 | 0.398 | 0.315 | 0.316 | 0.815 | 0.277 | 0.261 | 0.083 |
| rs1747815 | 0.005 | 0.326 | 0.332 | 0.432 | 0.311 | 0.312 | 0.813 | 0.270 | 0.256 | 0.135 |
| rs1775454 | 0.010 | 0.316 | 0.324 | 0.225 | 0.303 | 0.305 | 0.628 | 0.269 | 0.252 | 0.053 |
| rs1775456 | 0.012 | 0.319 | 0.329 | 0.163 | 0.303 | 0.309 | 0.338 | 0.263 | 0.251 | 0.212 |
| rs1924518 | 0.001 | 0.325 | 0.331 | 0.431 | 0.309 | 0.311 | 0.768 | 0.269 | 0.256 | 0.135 |
| rs1775444 | 0.002 | 0.326 | 0.332 | 0.395 | 0.309 | 0.312 | 0.723 | 0.267 | 0.254 | 0.171 |
| rs12026183 | 0.003 | 0.305 | 0.311 | 0.364 | 0.285 | 0.289 | 0.373 | 0.232 | 0.229 | 0.763 |
| rs10922300 | 0.004 | 0.274 | 0.286 | 0.068 | 0.258 | 0.266 | 0.096 | 0.216 | 0.213 | 0.871 |
| rs10922326 | 0.001 | 0.265 | 0.271 | 0.297 | 0.248 | 0.254 | 0.193 | 0.206 | 0.209 | 0.621 |

O(HET) observed heterozygosity; E(HET) expected heterozygosity.

TABLE 6

Imputed SNPs at the 1q31 locus. P-values and odds ratios of the associated SNPs imputed from the HapMap phased chromosomes in the EACHOP discovery cohort.

| Origin | SNP | Position | Allele | Posterior call | info | Control MAF | Case MAF | Missing data | OR | P-value |
|---|---|---|---|---|---|---|---|---|---|---|
| Imputed | rs2821125 | 195578785 | C | 0.996 | 0.991 | 0.223 | 0.152 | 0.008 | 0.623 | $7.05 \times 10^{-9}$ |
| Imputed | rs1337168 | 195582862 | C | 0.997 | 0.992 | 0.223 | 0.152 | 0.008 | 0.624 | $7.23 \times 10^{-9}$ |
| Imputed | rs1337167 | 195583058 | T | 0.997 | 0.992 | 0.223 | 0.152 | 0.008 | 0.624 | $7.26 \times 10^{-9}$ |
| Imputed | rs2786101 | 195587409 | T | 0.997 | 0.993 | 0.224 | 0.152 | 0.006 | 0.623 | $7.61 \times 10^{-9}$ |
| Genotyped | rs2786098 | 195592531 | T | 0.997 | 1.000 | 0.222 | 0.152 | 0.003 | 0.629 | $7.30 \times 10^{-9}$ |
| Imputed | rs2821116 | 195595664 | A | 0.998 | 0.995 | 0.224 | 0.153 | 0.006 | 0.627 | $8.17 \times 10^{-9}$ |
| Imputed | rs2786119 | 195596158 | A | 0.998 | 0.995 | 0.224 | 0.153 | 0.006 | 0.627 | $8.19 \times 10^{-9}$ |
| Imputed | rs2786117 | 195598780 | A | 0.998 | 0.995 | 0.224 | 0.153 | 0.006 | 0.627 | $8.19 \times 10^{-9}$ |
| Imputed | rs10801603 | 195604453 | G | 0.998 | 0.994 | 0.224 | 0.153 | 0.006 | 0.627 | $8.49 \times 10^{-9}$ |
| Imputed | rs2821107 | 195610573 | T | 0.996 | 0.991 | 0.224 | 0.153 | 0.013 | 0.627 | $1.44 \times 10^{-8}$ |
| Imputed | rs2759656 | 195619592 | A | 0.996 | 0.990 | 0.224 | 0.154 | 0.015 | 0.627 | $1.43 \times 10^{-8}$ |
| Imputed | rs2821103 | 195621187 | A | 0.988 | 0.953 | 0.132 | 0.092 | 0.037 | 0.664 | $2.22 \times 10^{-5}$ |
| Imputed | rs2759661 | 195629931 | G | 0.998 | 0.996 | 0.223 | 0.156 | 0.007 | 0.642 | $1.29 \times 10^{-8}$ |
| Imputed | rs2476019 | 195632766 | C | 0.998 | 0.996 | 0.223 | 0.156 | 0.007 | 0.642 | $1.29 \times 10^{-8}$ |
| Imputed | rs2821132 | 195646465 | T | 0.998 | 0.996 | 0.223 | 0.155 | 0.006 | 0.640 | $1.33 \times 10^{-8}$ |
| Genotyped | rs2821106 | 195650908 | T | 1.000 | 1.000 | 0.134 | 0.094 | 0.000 | 0.668 | $3.62 \times 10^{-5}$ |
| Genotyped | rs12134409 | 195658690 | T | 0.993 | 1.000 | 0.220 | 0.153 | 0.007 | 0.643 | $3.55 \times 10^{-8}$ |
| Imputed | rs17554990 | 195662731 | A | 0.998 | 0.996 | 0.223 | 0.155 | 0.006 | 0.641 | $1.43 \times 10^{-8}$ |
| Imputed | rs6685222 | 195675283 | T | 0.998 | 0.996 | 0.223 | 0.155 | 0.006 | 0.641 | $1.43 \times 10^{-8}$ |
| Imputed | rs17555558 | 195679789 | A | 0.937 | 0.870 | 0.257 | 0.177 | 0.214 | 0.622 | $6.28 \times 10^{-8}$ |
| Imputed | rs10922234 | 195702662 | G | 0.996 | 0.991 | 0.214 | 0.152 | 0.011 | 0.658 | $7.47 \times 10^{-8}$ |
| Imputed | rs12023045 | 195718785 | G | 0.996 | 0.991 | 0.214 | 0.152 | 0.012 | 0.658 | $8.04 \times 10^{-8}$ |
| Imputed | rs12563307 | 195719826 | A | 0.995 | 0.990 | 0.214 | 0.152 | 0.014 | 0.661 | $8.06 \times 10^{-8}$ |
| Imputed | rs12133659 | 195741277 | A | 0.995 | 0.983 | 0.133 | 0.094 | 0.015 | 0.677 | $5.49 \times 10^{-5}$ |

TABLE 6-continued

Imputed SNPs at the 1q31 locus. P-values and odds ratios of the associated SNPs imputed from the HapMap phased chromosomes in the EACHOP discovery cohort.

| Origin | SNP | Position | Allele | Posterior call | info | Control MAF | Case MAF | Missing data | OR | P-value |
|---|---|---|---|---|---|---|---|---|---|---|
| Imputed | rs12132165 | 195744908 | A | 0.995 | 0.984 | 0.134 | 0.095 | 0.013 | 0.679 | $5.69 \times 10^{-5}$ |
| Imputed | rs4915550 | 195774888 | A | 0.998 | 0.995 | 0.210 | 0.147 | 0.007 | 0.647 | $4.82 \times 10^{-8}$ |
| Genotyped | rs4915551 | 195775524 | G | 1.000 | 1.000 | 0.231 | 0.179 | 0.000 | 0.729 | $3.12 \times 10^{-5}$ |
| Imputed | rs4915552 | 195779401 | A | 1.000 | 0.999 | 0.210 | 0.148 | 0.001 | 0.653 | $1.25 \times 10^{-7}$ |
| Imputed | rs10754224 | 195779412 | A | 1.000 | 0.999 | 0.210 | 0.148 | 0.001 | 0.653 | $1.25 \times 10^{-7}$ |
| Imputed | rs4316386 | 195782400 | A | 1.000 | 0.999 | 0.210 | 0.148 | 0.001 | 0.653 | $1.25 \times 10^{-7}$ |
| Imputed | rs10922251 | 195788433 | G | 0.996 | 0.988 | 0.204 | 0.144 | 0.011 | 0.656 | $9.60 \times 10^{-8}$ |
| Imputed | rs6677361 | 195788500 | T | 0.996 | 0.988 | 0.204 | 0.144 | 0.011 | 0.656 | $9.60 \times 10^{-8}$ |
| Imputed | rs12028758 | 195789581 | T | 1.000 | 0.999 | 0.210 | 0.148 | 0.001 | 0.653 | $1.25 \times 10^{-7}$ |
| Imputed | rs10922253 | 195794238 | G | 0.981 | 0.955 | 0.230 | 0.161 | 0.059 | 0.641 | $2.92 \times 10^{-7}$ |
| Imputed | rs10494758 | 195794772 | G | 1.000 | 0.999 | 0.210 | 0.148 | 0.001 | 0.653 | $1.25 \times 10^{-7}$ |
| Genotyped | rs2111931 | 195795841 | C | 1.000 | 1.000 | 0.209 | 0.148 | 0.000 | 0.653 | $1.16 \times 10^{-7}$ |
| Imputed | rs1421397 | 195800977 | T | 1.000 | 0.999 | 0.210 | 0.148 | 0.001 | 0.653 | $1.26 \times 10^{-7}$ |
| Imputed | rs6689216 | 195802848 | A | 1.000 | 0.999 | 0.210 | 0.148 | 0.001 | 0.653 | $1.25 \times 10^{-7}$ |
| Imputed | rs10922255 | 195803652 | C | 1.000 | 0.999 | 0.210 | 0.148 | 0.001 | 0.653 | $1.25 \times 10^{-7}$ |
| Imputed | rs10922256 | 195811930 | T | 1.000 | 0.999 | 0.210 | 0.148 | 0.001 | 0.653 | $1.25 \times 10^{-7}$ |
| Imputed | rs10922257 | 195812343 | A | 1.000 | 0.999 | 0.210 | 0.148 | 0.001 | 0.653 | $1.25 \times 10^{-7}$ |
| Imputed | rs6676073 | 195813049 | T | 1.000 | 0.999 | 0.210 | 0.148 | 0.001 | 0.653 | $1.25 \times 10^{-7}$ |
| Genotyped | rs10737692 | 195815556 | A | 1.000 | 1.000 | 0.210 | 0.149 | 0.000 | 0.658 | $1.84 \times 10^{-7}$ |
| Imputed | rs4915555 | 195818137 | G | 1.000 | 0.999 | 0.210 | 0.148 | 0.001 | 0.653 | $1.26 \times 10^{-7}$ |
| Imputed | rs12131160 | 195822142 | C | 1.000 | 0.999 | 0.210 | 0.148 | 0.001 | 0.653 | $1.26 \times 10^{-7}$ |
| Imputed | rs2193734 | 195824175 | G | 1.000 | 0.999 | 0.210 | 0.148 | 0.001 | 0.653 | $1.26 \times 10^{-7}$ |
| Imputed | rs8179369 | 195828030 | T | 1.000 | 0.999 | 0.210 | 0.148 | 0.001 | 0.653 | $1.26 \times 10^{-7}$ |
| Imputed | rs12747786 | 195832455 | C | 1.000 | 0.999 | 0.210 | 0.148 | 0.001 | 0.653 | $1.26 \times 10^{-7}$ |
| Imputed | rs6428411 | 195836280 | A | 0.987 | 0.971 | 0.185 | 0.132 | 0.038 | 0.670 | $8.38 \times 10^{-7}$ |
| Imputed | rs6428412 | 195836641 | A | 0.933 | 0.852 | 0.198 | 0.147 | 0.208 | 0.702 | $1.09 \times 10^{-7}$ |
| Imputed | rs1833464 | 195838200 | G | 0.998 | 0.997 | 0.209 | 0.147 | 0.004 | 0.653 | $1.13 \times 10^{-7}$ |
| Imputed | rs1362939 | 195846707 | C | 1.000 | 1.000 | 0.216 | 0.156 | 0.000 | 0.670 | $3.61 \times 10^{-7}$ |
| Imputed | rs12116508 | 195847075 | C | 1.000 | 1.000 | 0.216 | 0.156 | 0.000 | 0.670 | $3.61 \times 10^{-7}$ |
| Imputed | rs4915557 | 195849224 | G | 1.000 | 1.000 | 0.216 | 0.156 | 0.000 | 0.670 | $3.61 \times 10^{-7}$ |
| Imputed | rs4915558 | 195849432 | T | 1.000 | 1.000 | 0.216 | 0.156 | 0.000 | 0.670 | $3.61 \times 10^{-7}$ |
| Imputed | rs3814321 | 195850466 | T | 1.000 | 1.000 | 0.216 | 0.156 | 0.000 | 0.670 | $3.61 \times 10^{-7}$ |
| Imputed | rs12133885 | 195859191 | T | 1.000 | 1.000 | 0.216 | 0.156 | 0.000 | 0.670 | $3.61 \times 10^{-7}$ |
| Genotyped | rs12127378 | 195867715 | C | 0.995 | 1.000 | 0.215 | 0.155 | 0.005 | 0.669 | $3.65 \times 10^{-7}$ |
| Genotyped | rs12041661 | 195868291 | A | 0.996 | 1.000 | 0.215 | 0.156 | 0.004 | 0.672 | $4.50 \times 10^{-7}$ |
| Genotyped | rs10442656 | 195873331 | T | 1.000 | 1.000 | 0.217 | 0.157 | 0.000 | 0.673 | $4.58 \times 10^{-7}$ |
| Genotyped | rs2477070 | 195879382 | G | 1.000 | 1.000 | 0.216 | 0.155 | 0.000 | 0.666 | $2.44 \times 10^{-7}$ |
| Genotyped | rs1747827 | 195882014 | T | 0.998 | 1.000 | 0.216 | 0.156 | 0.002 | 0.672 | $4.61 \times 10^{-7}$ |
| Imputed | rs1775453 | 195895965 | C | 0.995 | 0.988 | 0.240 | 0.177 | 0.011 | 0.678 | $5.43 \times 10^{-7}$ |
| Imputed | rs2488409 | 195911204 | T | 0.997 | 0.992 | 0.213 | 0.154 | 0.005 | 0.676 | $4.11 \times 10^{-7}$ |
| Imputed | rs2488410 | 195917128 | A | 1.000 | 1.000 | 0.216 | 0.155 | 0.000 | 0.668 | $2.86 \times 10^{-7}$ |
| Imputed | rs1775450 | 195919225 | T | 1.000 | 1.000 | 0.216 | 0.155 | 0.000 | 0.668 | $2.82 \times 10^{-7}$ |
| Imputed | rs1747811 | 195919659 | T | 1.000 | 1.000 | 0.216 | 0.155 | 0.000 | 0.668 | $2.81 \times 10^{-7}$ |
| Imputed | rs1578720 | 195923772 | G | 1.000 | 1.000 | 0.216 | 0.155 | 0.000 | 0.667 | $2.75 \times 10^{-7}$ |
| Genotyped | rs2488411 | 195925422 | C | 0.999 | 1.000 | 0.217 | 0.155 | 0.001 | 0.663 | $1.91 \times 10^{-7}$ |
| Genotyped | rs1891497 | 195926178 | A | 0.994 | 1.000 | 0.215 | 0.155 | 0.006 | 0.666 | $2.91 \times 10^{-7}$ |
| Imputed | rs2358774 | 195931018 | G | 1.000 | 1.000 | 0.216 | 0.155 | 0.000 | 0.667 | $2.72 \times 10^{-7}$ |
| Imputed | rs1573098 | 195950430 | G | 1.000 | 1.000 | 0.216 | 0.155 | 0.000 | 0.667 | $2.72 \times 10^{-7}$ |
| Imputed | rs1621898 | 195951122 | T | 1.000 | 1.000 | 0.216 | 0.155 | 0.000 | 0.667 | $2.72 \times 10^{-7}$ |
| Imputed | rs1775457 | 195951774 | C | 1.000 | 1.000 | 0.216 | 0.155 | 0.000 | 0.667 | $2.73 \times 10^{-7}$ |
| Imputed | rs2147300 | 195959750 | G | 0.999 | 0.998 | 0.216 | 0.154 | 0.005 | 0.661 | $2.20 \times 10^{-7}$ |
| Imputed | rs2488387 | 195960660 | A | 0.975 | 0.944 | 0.227 | 0.162 | 0.084 | 0.660 | $1.99 \times 10^{-7}$ |
| Genotyped | rs1747815 | 195964726 | T | 1.000 | 1.000 | 0.213 | 0.151 | 0.000 | 0.656 | $1.19 \times 10^{-7}$ |
| Imputed | rs1747814 | 195966322 | C | 0.936 | 0.863 | 0.200 | 0.138 | 0.184 | 0.643 | $3.36 \times 10^{-8}$ |
| Imputed | rs2488400 | 195968848 | G | 1.000 | 0.999 | 0.213 | 0.151 | 0.001 | 0.656 | $1.15 \times 10^{-7}$ |
| Imputed | rs1747817 | 195978115 | C | 0.988 | 0.974 | 0.227 | 0.161 | 0.035 | 0.652 | $7.08 \times 10^{-8}$ |
| Imputed | rs1775441 | 195978291 | T | 0.988 | 0.974 | 0.227 | 0.161 | 0.035 | 0.652 | $7.05 \times 10^{-8}$ |
| Imputed | rs1775442 | 195979023 | A | 0.988 | 0.974 | 0.227 | 0.161 | 0.035 | 0.652 | $7.08 \times 10^{-8}$ |
| Genotyped | rs1775454 | 195993921 | T | 0.996 | 1.000 | 0.206 | 0.146 | 0.004 | 0.660 | $2.92 \times 10^{-7}$ |
| Genotyped | rs1775456 | 195999678 | G | 0.991 | 1.000 | 0.209 | 0.147 | 0.009 | 0.653 | $1.40 \times 10^{-7}$ |
| Imputed | rs1342696 | 196000076 | G | 1.000 | 1.000 | 0.212 | 0.149 | 0.000 | 0.652 | $8.63 \times 10^{-8}$ |
| Imputed | rs1539413 | 196000565 | C | 1.000 | 1.000 | 0.212 | 0.149 | 0.000 | 0.652 | $8.63 \times 10^{-8}$ |
| Imputed | rs2488394 | 196002120 | C | 1.000 | 1.000 | 0.212 | 0.149 | 0.000 | 0.652 | $8.63 \times 10^{-8}$ |
| Genotyped | rs1924518 | 196004950 | A | 1.000 | 1.000 | 0.212 | 0.149 | 0.000 | 0.652 | $8.63 \times 10^{-8}$ |
| Imputed | rs2488395 | 196005403 | T | 1.000 | 1.000 | 0.212 | 0.149 | 0.000 | 0.652 | $8.63 \times 10^{-8}$ |
| Genotyped | rs1775444 | 196007313 | T | 1.000 | 1.000 | 0.212 | 0.149 | 0.000 | 0.652 | $8.63 \times 10^{-8}$ |
| Imputed | rs2488396 | 196008794 | C | 1.000 | 1.000 | 0.212 | 0.149 | 0.000 | 0.652 | $8.75 \times 10^{-8}$ |
| Imputed | rs1342694 | 196016491 | C | 1.000 | 1.000 | 0.212 | 0.149 | 0.001 | 0.653 | $8.82 \times 10^{-8}$ |
| Imputed | rs2477069 | 196018105 | A | 1.000 | 1.000 | 0.212 | 0.149 | 0.001 | 0.653 | $8.88 \times 10^{-8}$ |
| Imputed | rs1775469 | 196019697 | A | 1.000 | 1.000 | 0.212 | 0.149 | 0.001 | 0.653 | $8.88 \times 10^{-8}$ |
| Imputed | rs1747825 | 196019759 | C | 1.000 | 1.000 | 0.212 | 0.149 | 0.001 | 0.653 | $8.88 \times 10^{-8}$ |
| Imputed | rs1775468 | 196020687 | C | 1.000 | 1.000 | 0.212 | 0.149 | 0.001 | 0.653 | $8.88 \times 10^{-8}$ |
| Imputed | rs1775467 | 196021570 | A | 1.000 | 1.000 | 0.212 | 0.149 | 0.001 | 0.653 | $8.88 \times 10^{-8}$ |
| Imputed | rs1775466 | 196021590 | A | 1.000 | 1.000 | 0.212 | 0.149 | 0.001 | 0.653 | $8.88 \times 10^{-8}$ |

TABLE 6-continued

Imputed SNPs at the 1q31 locus. P-values and odds ratios of the associated SNPs imputed from the HapMap phased chromosomes in the EACHOP discovery cohort.

| Origin | SNP | Position | Allele | Posterior call | info | Control MAF | Case MAF | Missing data | OR | P-value |
|---|---|---|---|---|---|---|---|---|---|---|
| Imputed | rs1775465 | 196021966 | G | 1.000 | 1.000 | 0.212 | 0.149 | 0.001 | 0.653 | $8.82 \times 10^{-8}$ |
| Imputed | rs1775464 | 196021987 | T | 1.000 | 1.000 | 0.212 | 0.149 | 0.001 | 0.653 | $8.82 \times 10^{-8}$ |
| Imputed | rs1747823 | 196022269 | C | 1.000 | 1.000 | 0.212 | 0.149 | 0.001 | 0.653 | $8.88 \times 10^{-8}$ |
| Imputed | rs2454640 | 196032627 | T | 1.000 | 1.000 | 0.212 | 0.149 | 0.001 | 0.653 | $8.82 \times 10^{-8}$ |
| Imputed | rs1499593 | 196035130 | C | 1.000 | 1.000 | 0.212 | 0.149 | 0.001 | 0.653 | $8.82 \times 10^{-8}$ |
| Imputed | rs10922288 | 196036163 | C | 1.000 | 1.000 | 0.212 | 0.149 | 0.001 | 0.653 | $8.82 \times 10^{-8}$ |
| Imputed | rs12740849 | 196036444 | T | 0.912 | 0.777 | 0.107 | 0.083 | 0.253 | 0.754 | $1.95 \times 10^{-5}$ |
| Imputed | rs2133536 | 196040910 | T | 1.000 | 1.000 | 0.212 | 0.149 | 0.001 | 0.653 | $8.82 \times 10^{-8}$ |
| Imputed | rs12125742 | 196047367 | C | 1.000 | 1.000 | 0.212 | 0.149 | 0.001 | 0.653 | $8.82 \times 10^{-8}$ |
| Imputed | rs4915566 | 196049359 | C | 1.000 | 1.000 | 0.212 | 0.149 | 0.001 | 0.653 | $8.82 \times 10^{-8}$ |
| Imputed | rs6428417 | 196054342 | C | 1.000 | 1.000 | 0.212 | 0.149 | 0.001 | 0.653 | $8.82 \times 10^{-8}$ |
| Imputed | rs10922294 | 196057566 | A | 1.000 | 1.000 | 0.212 | 0.149 | 0.001 | 0.653 | $8.82 \times 10^{-8}$ |
| Imputed | rs6697696 | 196058878 | G | 1.000 | 1.000 | 0.212 | 0.149 | 0.001 | 0.653 | $8.82 \times 10^{-8}$ |
| Imputed | rs6704186 | 196060310 | C | 1.000 | 1.000 | 0.212 | 0.149 | 0.001 | 0.653 | $8.82 \times 10^{-8}$ |
| Imputed | rs4915569 | 196061641 | C | 1.000 | 1.000 | 0.212 | 0.149 | 0.001 | 0.653 | $8.81 \times 10^{-8}$ |
| Imputed | rs12140293 | 196076702 | A | 0.999 | 0.998 | 0.196 | 0.132 | 0.001 | 0.621 | $2.17 \times 10^{-8}$ |
| Imputed | rs12118454 | 196077272 | T | 0.979 | 0.945 | 0.164 | 0.117 | 0.063 | 0.677 | $1.74 \times 10^{-7}$ |
| Genotyped | rs12026183 | 196079655 | T | 1.000 | 1.000 | 0.196 | 0.131 | 0.000 | 0.618 | $1.10 \times 10^{-8}$ |
| Genotyped | rs10922300 | 196081308 | T | 0.999 | 1.000 | 0.174 | 0.121 | 0.001 | 0.654 | $1.35 \times 10^{-6}$ |
| Imputed | rs10801625 | 196081382 | A | 0.999 | 0.997 | 0.206 | 0.141 | 0.003 | 0.636 | $2.92 \times 10^{-8}$ |
| Imputed | rs10922304 | 196087568 | A | 0.996 | 0.989 | 0.201 | 0.142 | 0.015 | 0.657 | $3.89 \times 10^{-8}$ |
| Imputed | rs10922305 | 196088392 | C | 0.998 | 0.995 | 0.206 | 0.142 | 0.006 | 0.639 | $2.30 \times 10^{-8}$ |
| Genotyped | rs1499602 | 196109827 | C | 0.999 | 1.000 | 0.398 | 0.341 | 0.001 | 0.783 | $9.58 \times 10^{-5}$ |
| Genotyped | rs10801629 | 196110990 | T | 1.000 | 1.000 | 0.427 | 0.369 | 0.000 | 0.783 | $7.54 \times 10^{-5}$ |
| Imputed | rs10801632 | 196122786 | A | 0.997 | 0.996 | 0.398 | 0.341 | 0.008 | 0.783 | $8.92 \times 10^{-5}$ |
| Imputed | rs9662705 | 196130037 | T | 0.998 | 0.997 | 0.398 | 0.341 | 0.006 | 0.784 | $9.77 \times 10^{-5}$ |
| Genotyped | rs10922326 | 196134285 | G | 1.000 | 1.000 | 0.165 | 0.119 | 0.000 | 0.683 | $1.70 \times 10^{-5}$ |

TABLE 7

Comparative association at the 1q31 locus in the Caucasian cohorts; the Replication cohort (Rep) consisted of the Danish (COPSAC), German (MAGIC/ISAAC) and British (MRCA) cohorts compared to the discovery cohort (Disc).

| SNP | Pos | A1 | Disc case MAF | Disc control MAF | Disc P | Disc OR | Rep case MAF | Rep control MAF |
|---|---|---|---|---|---|---|---|---|
| rs2786098 | 194057565 | A | 0.152 | 0.222 | $8.55 \times 10^{-9}$ | 0.629 | 0.183 | 0.225 |
| rs2821106 | 194115942 | A | 0.0927 | 0.134 | $2.06 \times 10^{-5}$ | 0.658 | 0.113 | 0.136 |
| rs12134409 | 194123724 | T | 0.153 | 0.220 | $2.72 \times 10^{-8}$ | 0.639 | 0.186 | 0.229 |
| rs2111931 | 194260875 | C | 0.147 | 0.210 | $8.71 \times 10^{-8}$ | 0.649 | 0.175 | 0.209 |
| rs10737692 | 194280590 | A | 0.148 | 0.210 | $1.40 \times 10^{-7}$ | 0.654 | 0.176 | 0.209 |
| rs12127378 | 194332749 | C | 0.155 | 0.216 | $2.84 \times 10^{-7}$ | 0.665 | 0.182 | 0.215 |
| rs12041661 | 194333325 | A | 0.155 | 0.215 | $3.50 \times 10^{-7}$ | 0.668 | 0.182 | 0.214 |
| rs10442656 | 194338365 | T | 0.156 | 0.217 | $3.58 \times 10^{-7}$ | 0.670 | 0.182 | 0.214 |
| rs2477070 | 194344416 | G | 0.154 | 0.216 | $1.89 \times 10^{-7}$ | 0.662 | 0.182 | 0.214 |
| rs1747827 | 194347048 | T | 0.155 | 0.216 | $3.60 \times 10^{-7}$ | 0.668 | 0.182 | 0.215 |
| rs2488411 | 194390456 | C | 0.154 | 0.217 | $1.48 \times 10^{-7}$ | 0.659 | 0.182 | 0.214 |
| rs1891497 | 194391212 | A | 0.154 | 0.216 | $2.03 \times 10^{-7}$ | 0.661 | 0.182 | 0.214 |
| rs1747815 | 194429760 | A | 0.150 | 0.213 | $8.05 \times 10^{-8}$ | 0.651 | 0.180 | 0.209 |
| rs1775454 | 194458955 | T | 0.146 | 0.207 | $1.96 \times 10^{-7}$ | 0.655 | 0.165 | 0.181 |
| rs1775456 | 194464712 | G | 0.147 | 0.210 | $8.45 \times 10^{-8}$ | 0.647 | 0.179 | 0.203 |
| rs1924518 | 194469984 | A | 0.149 | 0.213 | $5.81 \times 10^{-8}$ | 0.647 | 0.192 | 0.217 |
| rs1775444 | 194472347 | T | 0.149 | 0.213 | $5.81 \times 10^{-8}$ | 0.647 | 0.179 | 0.203 |
| rs12026183 | 194544689 | T | 0.131 | 0.197 | $1.06 \times 10^{-8}$ | 0.616 | 0.161 | 0.181 |
| rs10922300 | 194546342 | T | 0.120 | 0.174 | $1.01 \times 10^{-6}$ | 0.649 | 0.135 | 0.166 |
| rs10922326 | 194599319 | G | 0.117 | 0.165 | $9.81 \times 10^{-6}$ | 0.674 | 0.127 | 0.148 |

| SNP | Rep P | Rep OR | Fisher's combined P | Fixed effect P | Fixed effect OR (95% CI) |
|---|---|---|---|---|---|
| rs2786098 | $6.47 \times 10^{-4}$ | 0.773 | $3.91 \times 10^{-11}$ | $9.33 \times 10^{-11}$ | 0.702 (0.630-0.781) |
| rs2821106 | $1.81 \times 10^{-3}$ | 0.814 | $1.81 \times 10^{-7}$ | $6.32 \times 10^{-06}$ | 0.734 (0.642-0.839) |
| rs12134409 | $5.37 \times 10^{-4}$ | 0.771 | $9.98 \times 10^{-11}$ | $1.64 \times 10^{-10}$ | 0.707 (0.636-0.786) |
| rs2111931 | $3.21 \times 10^{-3}$ | 0.691 | $1.70 \times 10^{-9}$ | $4.58 \times 10^{-9}$ | 0.658 (0.572-0.757) |
| rs10737692 | $3.47 \times 10^{-3}$ | 0.691 | $2.90 \times 10^{-9}$ | $6.95 \times 10^{-9}$ | 0.662 (0.576-0.761) |
| rs12127378 | $5.84 \times 10^{-3}$ | 0.704 | $9.37 \times 10^{-9}$ | $1.83 \times 10^{-8}$ | 0.674 (0.587-0.773) |
| rs12041661 | $6.18 \times 10^{-3}$ | 0.705 | $1.21 \times 10^{-8}$ | $2.43 \times 10^{-8}$ | 0.676 (0.589-0.776) |
| rs10442656 | $6.16 \times 10^{-3}$ | 0.816 | $1.23 \times 10^{-8}$ | $4.69 \times 10^{-8}$ | 0.743 (0.668-0.827) |
| rs2477070 | $6.18 \times 10^{-3}$ | 0.816 | $6.70 \times 10^{-9}$ | $2.96 \times 10^{-8}$ | 0.739 (0.665-0.823) |
| rs1747827 | $5.87 \times 10^{-3}$ | 0.815 | $1.18 \times 10^{-8}$ | $4.45 \times 10^{-8}$ | 0.743 (0.667-0.826) |

TABLE 7-continued

Comparative association at the 1q31 locus in the Caucasian cohorts; the Replication cohort (Rep) consisted of the Danish (COPSAC), German (MAGIC/ISAAC) and British (MRCA) cohorts compared to the discovery cohort (Disc).

| | | | | | |
|---|---|---|---|---|---|
| rs2488411 | $6.04 \times 10^{-3}$ | 0.704 | $5.19 \times 10^{-9}$ | $1.05 \times 10^{-8}$ | 0.669 (0.583-0.768) |
| rs1891497 | $6.39 \times 10^{-3}$ | 0.705 | $7.40 \times 10^{-9}$ | $1.41 \times 10^{-8}$ | 0.671 (0.584-0.770) |
| rs1747815 | 0.017 | 0.832 | $7.63 \times 10^{-9}$ | $5.45 \times 10^{-8}$ | 0.742 (0.666-0.826) |
| rs1775454 | 0.057 | 0.899 | $5.74 \times 10^{-8}$ | $4.15 \times 10^{-6}$ | 0.769 (0.688-0.860) |
| rs1775456 | 0.043 | 0.859 | $1.98 \times 10^{-8}$ | $2.95 \times 10^{-7}$ | 0.753 (0.676-0.839) |
| rs1924518 | 0.071 | 0.733 | $2.22 \times 10^{-8}$ | $1.08 \times 10^{-8}$ | 0.664 (0.577-0.764) |
| rs1775444 | 0.043 | 0.860 | $1.40 \times 10^{-8}$ | $2.47 \times 10^{-7}$ | 0.753 (0.676-0.838) |
| rs12026183 | 0.025 | 0.863 | $1.59 \times 10^{-9}$ | $1.31 \times 10^{-7}$ | 0.735 (0.656-0.824) |
| rs10922300 | $3.16 \times 10^{-3}$ | 0.789 | $1.75 \times 10^{-8}$ | $8.11 \times 10^{-8}$ | 0.715 (0.632-0.808) |
| rs10922326 | $8.32 \times 10^{-3}$ | 0.704 | $3.82 \times 10^{-7}$ | $1.30 \times 10^{-6}$ | 0.679 (0.581-0.795) |

A1 minor allele. SNPs rs2786098 and rs12134409 were imputed in the MAGIC and MRCA cohorts. Combined P-values are given for both Fisher's method and a fixed-effect meta-analysis.

TABLE 8

Cochrane test for heterogeneity P-values for the fixed effect meta-analysis presented in Table 7

| SNP | Cochrane test for heterogeneity P-value |
|---|---|
| rs2786098 | 0.059 |
| rs2821106 | 0.122 |
| rs12134409 | 0.085 |
| rs2111931 | 0.712 |
| rs10737692 | 0.746 |
| rs12127378 | 0.737 |
| rs12041661 | 0.752 |
| rs10442656 | 0.069 |
| rs2477070 | 0.055 |
| rs1747827 | 0.068 |
| rs2488411 | 0.697 |
| rs1891497 | 0.704 |
| rs1747815 | 0.026 |
| rs1775454 | 0.06 |
| rs1775456 | 0.010 |
| rs1924518 | 0.480 |
| rs1775444 | 0.009 |
| rs12026183 | 0.004 |
| rs10922300 | 0.117 |
| rs10922326 | 0.824 |

TABLE 9

Individual P-values and ORs for the individual cohorts in the combined replication set.

| rs ID | COPSAC P-value | COPSAC OR | MAGIC P-value | MAGIC OR | MRCA P-value | MRCA OR |
|---|---|---|---|---|---|---|
| rs2786098 | 0.022 | 0.722 | 0.002 | 0.726 | 0.824 | 0.999 |
| rs2821106 | 0.091 | 0.765 | 0.001 | 0.660 | 0.514 | 0.892 |
| rs12134409 | 0.000 | 0.574 | 0.016 | 0.771 | 0.572 | 0.919 |
| rs2111931 | 0.020 | 0.721 | 0.074 | 0.829 | 0.421 | 0.882 |
| rs10737692 | 0.017 | 0.716 | 0.074 | 0.829 | 0.421 | 0.882 |
| rs12127378 | 0.013 | 0.705 | 0.124 | 0.854 | 0.783 | 0.959 |
| rs12041661 | 0.014 | 0.710 | 0.117 | 0.851 | 0.783 | 0.959 |
| rs10442656 | 0.014 | 0.711 | 0.107 | 0.847 | 0.758 | 0.954 |
| rs2477070 | 0.014 | 0.710 | 0.117 | 0.851 | 0.783 | 0.959 |
| rs1747827 | 0.014 | 0.710 | 0.100 | 0.844 | 0.783 | 0.959 |
| rs2488411 | 0.020 | 0.724 | 0.118 | 0.852 | 0.785 | 0.960 |
| rs1891497 | 0.029 | 0.737 | 0.072 | 0.830 | 0.792 | 0.961 |
| rs1747815 | 0.024 | 0.729 | 0.143 | 0.859 | 0.810 | 0.964 |
| rs1775454 | 0.061 | 0.764 | 0.304 | 0.956 | 0.996 | 0.963 |
| rs1775456 | 0.039 | 0.747 | 0.333 | 0.905 | 0.943 | 0.989 |
| rs1924518 | 0.039 | 0.747 | 0.505 | 0.929 | 0.971 | 0.987 |
| rs1775444 | 0.039 | 0.747 | 0.321 | 0.903 | 0.929 | 0.987 |
| rs12026183 | 0.007 | 0.675 | 0.545 | 0.971 | 0.492 | 0.898 |
| rs10922300 | 0.005 | 0.665 | 0.057 | 0.761 | 0.453 | 0.904 |
| rs10922326 | 0.017 | 0.689 | 0.379 | 0.955 | 0.461 | 0.809 |

TABLE 10

Odds ratios and P-values for the combined analysis of all European ancestry asthma samples

| Chr | Rsid | pos | allele_A | allele_B | all_OR | frequentist_add_proper |
|---|---|---|---|---|---|---|
| 1 | rs2821125 | 195578785 | C | G | 1.419 | 3.03E−09 |
| 1 | rs1337168 | 195582862 | C | G | 1.419 | 3.05E−09 |

TABLE 10-continued

Odds ratios and P-values for the combined analysis of all European ancestry asthma samples

| Chr | Rsid | pos | allele_A | allele_B | all_OR | frequentist_add_proper |
|---|---|---|---|---|---|---|
| 1 | rs1337167 | 195583058 | C | T | 0.705 | 3.09E−09 |
| 1 | rs2786101 | 195587409 | A | T | 0.705 | 3.06E−09 |
| 1 | rs2786098 | 195592531 | G | T | 0.705 | 3.04E−09 |
| 1 | rs2821116 | 195595664 | A | T | 1.419 | 2.99E−09 |
| 1 | rs2786119 | 195596158 | A | C | 1.419 | 2.98E−09 |
| 1 | rs2786117 | 195598780 | A | G | 1.419 | 3.01E−09 |
| 1 | rs2786116 | 195600402 | A | G | 0.705 | 3.09E−09 |
| 1 | rs10801603 | 195604453 | A | G | 0.705 | 2.96E−09 |
| 1 | rs2821107 | 195610573 | A | T | 0.720 | 4.61E−09 |
| 1 | rs2759656 | 195619592 | A | G | 1.388 | 4.66E−09 |
| 1 | rs2821103 | 195621187 | A | G | 1.398 | 6.31E−07 |
| 17 | rs1008723 | 35319793 | G | T | 0.795 | 9.05E−08 |
| 17 | rs10445308 | 35191573 | C | T | 0.806 | 3.84E−07 |
| 17 | rs1054609 | 35286803 | A | C | 0.798 | 1.74E−07 |
| 17 | rs10852936 | 35285240 | C | T | 0.798 | 1.73E−07 |
| 17 | rs11078925 | 35278734 | C | T | 1.255 | 1.71E−07 |
| 17 | rs11078926 | 35316502 | A | G | 1.274 | 2.60E−08 |
| 17 | rs11078927 | 35317931 | C | T | 0.783 | 2.36E−08 |
| 17 | rs11557466 | 35278152 | C | T | 0.797 | 1.71E−07 |
| 17 | rs11557467 | 35282160 | G | T | 0.806 | 8.21E−07 |
| 17 | rs11870965 | 35283731 | A | T | 1.254 | 1.72E−07 |
| 17 | rs12150079 | 35278943 | A | G | 1.241 | 5.59E−05 |
| 17 | rs12232497 | 35293645 | C | T | 1.254 | 1.77E−07 |
| 17 | rs12936231 | 35282646 | C | G | 0.806 | 7.18E−07 |
| 17 | rs12950743 | 35302759 | C | T | 1.236 | 7.54E−07 |
| 17 | rs2290400 | 35319766 | C | T | 1.274 | 3.22E−08 |
| 17 | rs2305479 | 35315743 | C | T | 0.798 | 1.21E−07 |
| 17 | rs2305480 | 35315722 | A | G | 1.278 | 3.31E−08 |
| 17 | rs2872507 | 35294289 | A | G | 1.254 | 1.77E−07 |
| 17 | rs3816470 | 35239327 | A | G | 0.826 | 6.61E−06 |
| 17 | rs4795397 | 35277271 | A | G | 0.797 | 1.71E−07 |
| 17 | rs4795400 | 35320546 | C | T | 0.783 | 2.08E−08 |
| 17 | rs7359623 | 35303115 | C | T | 0.835 | 2.55E−06 |
| 17 | rs8067378 | 35304874 | A | G | 0.803 | 5.27E−07 |
| 17 | rs8069176 | 35310723 | A | G | 1.275 | 5.84E−08 |
| 17 | rs869402 | 35321569 | C | T | 0.795 | 9.07E−08 |
| 17 | rs907091 | 35175268 | C | T | 1.234 | 1.71E−06 |
| 17 | rs907092 | 35175785 | A | G | 1.239 | 1.06E−06 |
| 17 | rs9303277 | 35229995 | C | T | 0.803 | 4.97E−07 |
| 17 | rs9901146 | 35296869 | A | G | 1.236 | 7.44E−07 |
| 17 | rs9907088 | 35288642 | A | G | 1.254 | 1.75E−07 |
| 17 | rs7216389 | 35323475 | C | T | 1.254 | 2.41E−07 |
| 17 | rs9303280 | 35327557 | C | T | 0.800 | 2.84E−07 |
| 17 | rs9303281 | 35327572 | A | G | 0.798 | 2.35E−07 |
| 17 | rs7219923 | 35328044 | C | T | 1.254 | 2.37E−07 |
| 17 | rs7224129 | 35328952 | A | G | 0.797 | 2.41E−07 |
| 17 | rs4378650 | 35334391 | A | G | 1.246 | 3.49E−07 |
| 17 | rs8076131 | 35334438 | A | G | 0.789 | 6.25E−08 |
| 17 | rs12603332 | 35336333 | C | T | 0.805 | 7.11E−07 |
| 17 | rs4795405 | 35341943 | C | T | 0.791 | 1.45E−07 |
| 17 | rs4794820 | 35342870 | A | G | 1.251 | 2.22E−07 |
| 17 | rs7207600 | 35345186 | A | G | 0.792 | 8.00E−07 |
| 17 | rs8079416 | 35346239 | C | T | 0.808 | 1.19E−06 |
| 17 | rs6503525 | 35348700 | C | G | 0.807 | 1.04E−06 |
| 17 | rs8065126 | 35352561 | C | T | 0.790 | 8.45E−07 |
| 17 | rs4065985 | 35355458 | C | G | 0.780 | 5.25E−07 |
| 17 | rs4795408 | 35361153 | A | G | 0.803 | 9.89E−07 |
| 17 | rs9895948 | 35361889 | C | T | 0.799 | 1.36E−06 |
| 17 | rs17609240 | 35364215 | G | T | 0.792 | 8.56E−07 |
| 17 | rs8076474 | 35364760 | C | G | 0.799 | 1.46E−06 |
| 17 | rs1007654 | 35364880 | A | G | 1.248 | 1.24E−06 |
| 17 | rs1007655 | 35364945 | A | G | 0.799 | 1.46E−06 |
| 17 | rs2313640 | 35365371 | C | T | 1.256 | 9.88E−07 |
| 17 | rs7218742 | 35367887 | A | G | 1.259 | 8.69E−07 |
| 17 | rs7218321 | 35367995 | C | T | 1.273 | 6.99E−07 |
| 17 | rs7219080 | 35368042 | A | C | 1.278 | 6.80E−07 |
| 17 | rs6503526 | 35368124 | C | T | 1.243 | 1.02E−06 |
| 17 | rs6503527 | 35368245 | A | G | 0.782 | 5.36E−07 |
| 17 | rs3902025 | 35372780 | G | T | 1.275 | 5.80E−08 |
| 17 | rs3894194 | 35375519 | A | G | 0.820 | 6.15E−06 |
| 17 | rs7212938 | 35376206 | G | T | 0.802 | 1.63E−06 |
| 6 | rs1033700 | 165960069 | C | T | 1.312 | 1.78E−05 |
| 6 | rs2983510 | 165963067 | A | G | 0.768 | 7.87E−05 |
| 6 | rs753759 | 165966401 | C | G | 0.758 | 1.40E−05 |
| 6 | rs3008042 | 165970952 | C | T | 1.331 | 9.47E−06 |

TABLE 10-continued

Odds ratios and P-values for the combined analysis of all European ancestry asthma samples

| Chr | Rsid | pos | allele_A | allele_B | all_OR | frequentist_add_proper |
|---|---|---|---|---|---|---|
| 6 | rs2983515 | 165971234 | A | C | 0.754 | 1.56E−05 |
| 6 | rs1358786 | 165974912 | A | G | 1.473 | 8.35E−08 |
| 6 | rs9348025 | 165976454 | A | C | 0.761 | 2.01E−05 |
| 3 | rs275358 | 81551603 | A | C | 0.813 | 3.68E−06 |
| 3 | rs276114 | 81560744 | A | T | 0.854 | 2.23E−04 |
| 3 | rs276117 | 81564719 | A | G | 1.170 | 2.66E−04 |
| 3 | rs276119 | 81566114 | C | G | 1.161 | 1.67E−03 |
| 3 | rs276123 | 81568696 | A | T | 0.851 | 2.08E−04 |
| 3 | rs276125 | 81571248 | C | T | 1.175 | 2.03E−04 |
| 3 | rs1675838 | 81575713 | G | T | 0.857 | 3.62E−04 |
| 3 | rs9843238 | 81577304 | C | T | 1.161 | 1.63E−03 |
| 3 | rs1677057 | 81577740 | C | T | 1.162 | 1.65E−03 |
| 3 | rs9309871 | 81579031 | A | C | 0.800 | 3.62E−03 |
| 3 | rs1461614 | 81580181 | C | T | 0.800 | 3.80E−07 |
| 3 | rs2372904 | 81581427 | A | G | 0.834 | 8.17E−05 |
| 9 | rs677302 | 9587252 | C | T | 0.822 | 2.08E−06 |
| 9 | rs677243 | 9587302 | C | G | 1.229 | 1.17E−06 |
| 9 | rs1412398 | 9589213 | C | T | 1.236 | 1.40E−06 |
| 9 | rs651116 | 9589450 | G | T | 0.815 | 8.65E−07 |
| 9 | rs664869 | 9590239 | G | T | 0.818 | 9.56E−07 |
| 9 | rs9407436 | 9590720 | A | C | 0.810 | 1.47E−06 |
| 9 | rs7046780 | 9592389 | G | T | 1.240 | 9.44E−07 |
| 9 | rs1326772 | 9592686 | A | C | 0.806 | 8.29E−07 |
| 9 | rs1326773 | 9592730 | C | G | 1.240 | 9.52E−07 |
| 9 | rs10977865 | 9593122 | A | T | 0.807 | 1.05E−06 |

TABLE 11

Associated SNP P-values and odds ratios in the North American European ancestry discovery cohort and the African American (AA) samples.

| SNP | bp | A1 | Disc case MAF | Disc control MAF | DiscP | Disc OR | A2 | AA case AAF | AA control AAF | AA P | AA OR | EA/AA Meta-analysis |
|---|---|---|---|---|---|---|---|---|---|---|---|---|
| rs2786098 | 194057565 | A | 0.152 | 0.222 | $8.55 \times 10^{-9}$ | 0.6293 | C | 0.902 | 0.928 | $3.77 \times 10^{-5}$ | 0.71 | $5.50 \times 10^{-12}$ |
| rs2821106 | 194115942 | A | 0.0927 | 0.134 | $2.06 \times 10^{-5}$ | 0.6581 | G | 0.974 | 0.987 | $3.52 \times 10^{-5}$ | 0.49 | $1.50 \times 10^{-8}$ |
| rs12134409 | 194123724 | T | 0.153 | 0.220 | $2.72 \times 10^{-8}$ | 0.6392 | C | 0.936 | 0.957 | $3.80 \times 10^{-5}$ | 0.66 | $2.10 \times 10^{-11}$ |
| rs2111931 | 194260875 | C | 0.147 | 0.210 | $8.71 \times 10^{-8}$ | 0.6488 | T | 0.775 | 0.803 | $3.32 \times 10^{-3}$ | 0.85 | $4.38 \times 10^{-9}$ |
| rs10737692 | 194280590 | A | 0.148 | 0.210 | $1.40 \times 10^{-7}$ | 0.6539 | G | 0.685 | 0.711 | 0.017 | 0.88 | $3.12 \times 10^{-8}$ |
| rs12127378 | 194332749 | C | 0.155 | 0.216 | $2.84 \times 10^{-7}$ | 0.6653 | T | 0.918 | 0.939 | $4.78 \times 10^{-4}$ | 0.73 | $2.60 \times 10^{-9}$ |
| rs12041661 | 194333325 | A | 0.155 | 0.215 | $3.50 \times 10^{-7}$ | 0.668 | C | 0.921 | 0.942 | $2.81 \times 10^{-4}$ | 0.72 | $1.98 \times 10^{-9}$ |
| rs10442656 | 194338365 | T | 0.156 | 0.217 | $3.58 \times 10^{-7}$ | 0.6696 | C | 0.767 | 0.775 | 0.429 | 0.96 | $1.05 \times 10^{-6}$ |
| rs2477070 | 194344416 | G | 0.154 | 0.216 | $1.89 \times 10^{-7}$ | 0.662 | A | 0.922 | 0.941 | $8.00 \times 10^{-4}$ | 0.74 | $2.76 \times 10^{-9}$ |
| rs1747827 | 194347048 | T | 0.155 | 0.216 | $3.60 \times 10^{-7}$ | 0.6684 | C | 0.921 | 0.941 | $5.09 \times 10^{-4}$ | 0.73 | $3.51 \times 10^{-9}$ |
| rs2488411 | 194390456 | C | 0.154 | 0.217 | $1.48 \times 10^{-7}$ | 0.6593 | T | 0.769 | 0.777 | 0.398 | 0.95 | $4.01 \times 10^{-7}$ |
| rs1891497 | 194391212 | A | 0.154 | 0.216 | $2.03 \times 10^{-7}$ | 0.6614 | G | 0.922 | 0.94 | $1.62 \times 10^{-3}$ | 0.76 | $5.66 \times 10^{-9}$ |
| rs1747815 | 194429760 | A | 0.150 | 0.213 | $8.05 \times 10^{-8}$ | 0.6508 | G | 0.949 | 0.972 | $3.14 \times 10^{-7}$ | 0.53 | $6.63 \times 10^{-13}$ |
| rs1775454 | 194458955 | T | 0.146 | 0.207 | $1.96 \times 10^{-7}$ | 0.655 | C | 0.844 | 0.857 | 0.119 | 0.9 | $2.22 \times 10^{-7}$ |
| rs1775456 | 194464712 | G | 0.147 | 0.210 | $8.45 \times 10^{-8}$ | 0.6467 | A | 0.95 | 0.973 | $4.27 \times 10^{-7}$ | 0.53 | $9.16 \times 10^{-13}$ |
| rs1924518 | 194469984 | A | 0.149 | 0.213 | $5.81 \times 10^{-8}$ | 0.6468 | G | 0.951 | 0.973 | $8.61 \times 10^{-7}$ | 0.53 | $1.25 \times 10^{-12}$ |
| rs1775444 | 194472347 | T | 0.149 | 0.213 | $5.81 \times 10^{-8}$ | 0.6468 | C | 0.951 | 0.973 | $9.43 \times 10^{-7}$ | 0.53 | $1.36 \times 10^{-12}$ |
| rs12026183 | 194544689 | T | 0.131 | 0.197 | $1.06 \times 10^{-8}$ | 0.6165 | C | 0.951 | 0.972 | $3.99 \times 10^{-6}$ | 0.55 | $7.54 \times 10^{-13}$ |
| rs10922300 | 194546342 | T | 0.120 | 0.174 | $1.01 \times 10^{-6}$ | 0.649 | C | 0.968 | 0.981 | $2.36 \times 10^{-4}$ | 0.59 | $3.95 \times 10^{-9}$ |
| rs10922326 | 194599319 | G | 0.117 | 0.165 | $9.81 \times 10^{-6}$ | 0.6736 | T | 0.945 | 0.965 | $3.20 \times 10^{-5}$ | 0.62 | $6.29 \times 10^{-9}$ |

A1 minor allele, A2 ancestral allele. MAF: Minor allele frequency. AAF: ancestral allele frequency. The reported ORs in the AA samples were calculated on the ancestral alleles.

TABLE 12

Age of onset analysis in the EA discovery cohort and AA.

| SNP | Position | EA anovaP | AA anovaP |
|---|---|---|---|
| rs2786098 | 194057565 | 0.058 | 0.086 |
| rs2821106 | 194115942 | 0.017 | 0.065 |
| rs12134409 | 194123724 | 0.324 | 0.061 |
| rs2111931 | 194260875 | 0.002 | 0.022 |
| rs10737692 | 194280590 | 0.016 | 0.015 |
| rs12127378 | 194332749 | 0.021 | 0.025 |
| rs12041661 | 194333325 | 0.025 | 0.078 |
| rs10442656 | 194338365 | 0.482 | 0.167 |
| rs2477070 | 194344416 | 0.012 | 0.105 |
| rs1747827 | 194347048 | 0.445 | 0.114 |
| rs2488411 | 194390456 | 0.094 | 0.237 |
| rs1891497 | 194391212 | 0.030 | 0.148 |
| rs1747815 | 194429760 | 0.274 | 0.124 |
| rs1775454 | 194458955 | 0.125 | 0.322 |

TABLE 12-continued

Age of onset analysis in the EA discovery cohort and AA.

| SNP | Position | EA anovaP | AA anovaP |
|---|---|---|---|
| rs1775456 | 194464712 | 0.027 | 0.166 |
| rs1924518 | 194469984 | 0.075 | 0.170 |
| rs1775444 | 194472347 | 0.024 | 0.121 |
| rs12026183 | 194544689 | 0.106 | 0.248 |
| rs10922300 | 194546342 | 0.084 | 0.316 |
| rs10922326 | 194599319 | 0.516 | 0.306 |

P-values of ANOVA on the log transformed ages of onset and the DENND1BSNP genotypes with additive encoding.

REFERENCES

1. Ober C, Hoffjan S. Asthma genetics 2006: the long and winding road to gene discovery. Genes Immun 2006; 7(2):95-100.
2. Vercelli D. Discovering susceptibility genes for asthma and allergy. Nature reviews 2008; 8(3):169-82.
3. Halapi E, Hakonarson H. Recent development in genomic and proteomic research for asthma. Curr Opin Pulm Med 2004; 10(1):22-30.
4. Martinez F D, Wright A L, Taussig L M, Holberg C J, Halonen M, Morgan W J. Asthma and wheezing in the first six years of life. The Group Health Medical Associates. N Engl J Med 1995; 332(3):133-8.
5. Sears M R, Greene J M, Willan A R, et al. A longitudinal, population-based, cohort study of childhood asthma followed to adulthood. N Engl J Med 2003; 349(15):1414-22.
6. Moffatt M, Kabesch M, Liang L, et al. Genetic variants regulating ORMDL3 expression contribute to the risk of childhood asthma. Nature 2007; 448(7152):470-3.
7. Genome-wide association study of 14,000 cases of seven common diseases and 3,000 shared controls. Nature 2007; 447(7145):661-78.
8. Kugathasan S, Baldassano R N, Bradfield J P, et al. Loci on 20q13 and 21q22 are associated with pediatric-onset inflammatory bowel disease. Nat Genet 2008; 40(10): 1211-5.
9. Zeggini E, Scott L, Saxena R, et al. Meta-analysis of genome-wide association data and large-scale replication identifies additional susceptibility loci for type 2 diabetes. Nat Genet 2008; 40(5):638-45.
10. Bouzigon E, Corda E, Aschard H, et al. Effect of 17q21 Variants and Smoking Exposure in Early-Onset Asthma. N Engl J Med 2008.
11. Expert Panel Report 3 (EPR-3): Guidelines for the Diagnosis and Management of Asthma-Summary Report 2007. J Allergy Clin Immunol 2007; 120(5 Suppl):S94-138.
12. Bisgaard H, Hermansen M, Buchvald F, et al. Childhood asthma after bacterial colonization of the airway in neonates. N Engl J Med 2007; 357(15):1487-95.
13. Bisgaard H, Hermansen M, Loland L, Halkjaer L, Buchvald F. Intermittent inhaled corticosteroids in infants with episodic wheezing. N Engl J Med 2006; 354(19): 1998-2005.
14. Falush D, Stephens M, Pritchard J. Inference of population structure using multilocus genotype data: linked loci and correlated allele frequencies. Genetics 2003; 164(4):1567-87.
15. Luca D, Ringquist S, Klei L, et al. On the use of general control samples for genome-wide association studies: genetic matching highlights causal variants. Am J Hum Genet 2008; 82(2):453-63.
16. Gunderson K, Steemers F, Lee G, Mendoza L, Chee M. A genome-wide scalable SNP genotyping assay using microarray technology. Nat Genet 2005; 37(5):549-54.
17. Steemers F, Chang W, Lee G, Barker D, Shen R, Gunderson K. Whole-genome genotyping with the single-base extension assay. Nat Methods 2006; 3(1):31-3.
18. Hakonarson H, Grant S, Bradfield J, et al. A genome-wide association study identifies KIAA0350 as a type 1 diabetes gene. Nature 2007; 448(7153):591-4.
19. J. Marchini, B. Howie, S. Myers, G. McVean and P. Donnelly (2007) A new multipoint method for genome-wide association studies via imputation of genotypes. Nature Genetics 39: 906-913.
20. Lin P, Vance J, Pericak-Vance M, Martin E. No gene is an island: the flip-flop phenomenon. Am J Hum Genet 2007; 80(3):531-8.
21. Gosens I, den Hollander A, Cremers F, Roepman R. Composition and function of the Crumbs protein complex in the mammalian retina. Exp Eye Res 2008.
22. den Hollander A, ten Brink J, de Kok Y, et al. Mutations in a human homologue of Drosophila crumbs cause retinitis pigmentosa (RP12). Nat Genet 1999; 23(2):217-21.
23. den Hollander A, Johnson K, de Kok Y, et al. CRB1 has a cytoplasmic domain that is functionally conserved between human and Drosophila. Hum Mol Genet 2001; 10(24):2767-73.
24. Del Villar K, Miller C. Down-regulation of DENN/MADD, a TNF receptor binding protein, correlates with neuronal cell death in Alzheimer's disease brain and hippocampal neurons. Proc Natl Acad Sci USA 2004; 101(12):4210-5.
25. Miyoshi J, Takai Y. Dual role of DENN/MADD (Rab3GEP) in neurotransmission and neuroprotection. Trends Mol Med 2004; 10(10):476-80.
26. Lindstedt M, Lundberg K, Borrebaeck C. Gene family clustering identifies functionally associated subsets of human in vivo blood and tonsillar dendritic cells. J Immunol 2005; 175(8):4839-46.
27. Su A, Cooke M, Ching K, et al. Large-scale analysis of the human and mouse transcriptomes. Proc Natl Acad Sci USA 2002; 99(7):4465-70.
28. Liu Y. Dendritic cell subsets and lineages, and their functions in innate and adaptive immunity. Cell 2001; 106(3):259-62.
29. Willinger T, Freeman T, Hasegawa H, McMichael A, Callan M. Molecular signatures distinguish human central memory from effector memory CD8 T cell subsets. J Immunol 2005; 175(9):5895-903.
30. Wills-Karp M, Ewart S. Time to draw breath: asthma-susceptibility genes are identified. Nat Rev Genet 2004; 5(5):376-87.
31. Galanter J, Choudhry S, Eng C, et al. ORMDL3 Gene is Associated with Asthma in Three Ethnically Diverse Populations. Am J Respir Crit Care Med 2008.
32. Tavendale R, Macgregor D, Mukhopadhyay S, Palmer C. A polymorphism controlling ORMDL3 expression is associated with asthma that is poorly controlled by current medications. J Allergy Clin Immunol 2008; 121(4):860-3.
33. Sleiman P M, Annaiah K, Imielinski M, et al. ORMDL3 variants associated with asthma susceptibility in North Americans of European ancestry. J Allergy Clin Immunol 2008.

EXAMPLE II

Diagnostic Methods for Asthma and Screening Assays to Identify Therapeutic Agents Useful for the Treatment of the Same The information herein above can be applied clinically to patients for diagnosing an increased susceptibility for developing early onset pediatric asthma, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing asthma. This can occur after a patient arrives in the clinic; the patient has blood drawn, and using the diagnostic methods described herein, a clinician can detect a SNP in the regions of chromosome 1 described herein. The typical age range for a patient to be screened is between 3 and 12 years of age. The information obtained from the patient sample, which can optionally be amplified prior to assessment, will be used to diagnose a patient with an increased or decreased susceptibility for developing asthma. Kits for performing the diagnostic method of the invention are also provided herein. Such kits comprise a microarray comprising at least one of the SNPs provided herein in and the necessary reagents for assessing the patient samples as described above.

The identity of asthma-involved genes and the patient results will indicate which variants are present, and will identify those that possess an altered risk for developing asthma. The information provided herein allows for therapeutic intervention at earlier times in disease progression that previously possible. Also as described herein above, DENND1B provides a novel target for the development of new therapeutic agents efficacious for the treatment of asthma.

Figure 5:
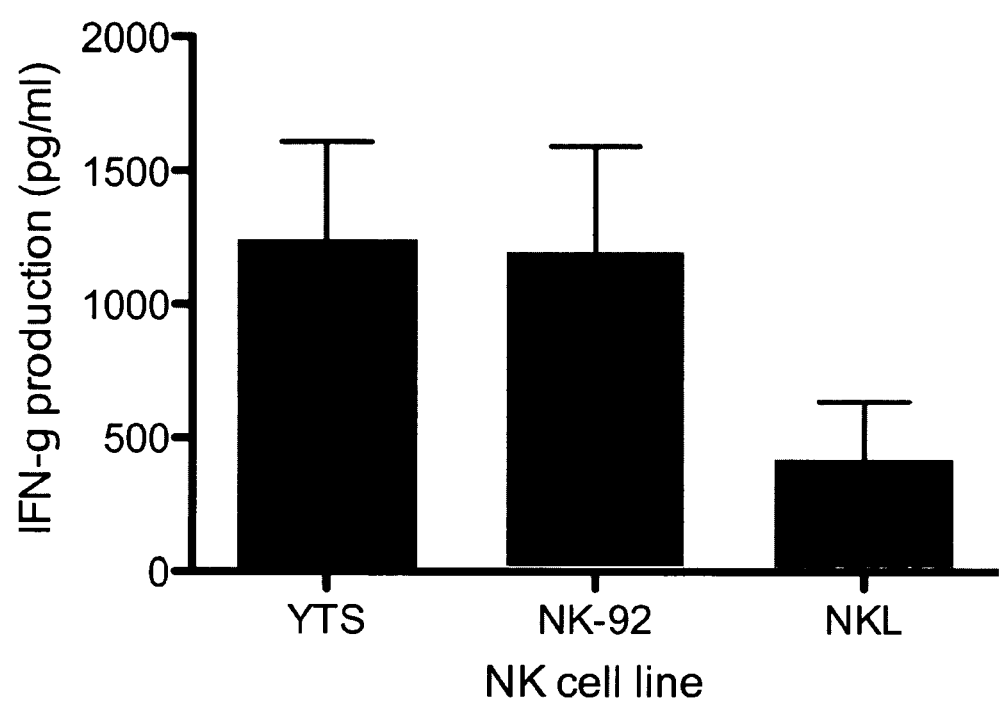
FIG. 5: Cells possessing different DENND1B alleles exhibit differential induced cytokine production in NK cell lines

We have observed differential induced cytokine production in NK cell lines possessing different DENND1B alleles. See FIG. 5. YTS, NK-92 and NKL cell lines were evaluated for their ability to produce IFN-γ after induction by a susceptible virally-transformed target cell. NK cells were mixed with the target cells for 18 h and then supernatants harvested and tested for the presence of IFN-γ by ELISA. Each bar represents the mean±SD of three independent experiments performed on separate dates. The difference between the NKL and other NK cell lines was significant p<0.01. The NKL cell line contains the DENND1B minor allele while the YTS and NK-92 lines contain the major allele. Natural killer cells (NK) cells are inflammatory cells that expresses DENND1B gene at higher levels than dendritic cells. Cells that carry the risk allele (major allele) secrete more interferon gamma when they are activated, than do NK cells that carry the protective (minor) allele. This implicates DENND1B in the regulation of cytokine production/release, and that the risk allele appears to dysregulate this process. Thus the different DENND1B alleles in NK cells are associated with differential ability to secrete cytokine after exposure to a standard uniform stimulus. Accordingly, down modulation of DENN1B activity should exhibit beneficial therapeutic affects and ameliorate asthmatic symptoms.

In particular, it would be desirable to block expression of this gene in those patients that are more prone to develop the disease. In this regard, the therapeutic siRNAs described herein can be used to block expression of the gene product based on the patient signal, thereby inhibiting the development of the asthmatic phenotype.

Candidate siRNA compositions for use in the invention are provided in Table 13. Those of skill in the art can determine the sequence of an antisense siRNA strand based on the disclosure of the sense strand, and will appreciate the difference between any "U" and "T" designations in the sequences which correspond to RNA and DNA molecules, respectively. Also, methods of using known agents for the treatment of asthma, e.g, glucocorticoids, are also provided. In addition, shRNA constructs can be designed based on the sense sequence provided in Table 13, and may be effective to inhibit DENND1B expression. The shRNA constructs utilizing the sense strand from Table 13 for the respective targets would include a hairpin loop 3' to the sense sequence (e.g., suitable hairpins include, but are not limited to: TCAAGAG, TTCAAGAGA, GAAGCTTG, and TTCG) followed by the corresponding antisense sequence from the sense strand provided in Table 13.

TABLE 13

| Candidate DENND1B siRNA Molecules (sense) | |
|---|---|
| TGACAGACATTGAAAGTAAtt | SEQ ID NO: 1 |
| CCTCATAGAGAGAGTGAAAtt | SEQ ID NO: 2 |
| GTGATTATCTCGAGCAAATtt | SEQ ID NO: 3 |
| GGAAGATGTTGTTATGTTAtt | SEQ ID NO: 4 |
| GCTCAAGCGTGATGAAACAtt | SEQ ID NO: 5 |
| GAGTGTGAACCAAGAGATAtt | SEQ ID NO: 6 |
| GAGTAGAAATCTTACAGAAtt | SEQ ID NO: 7 |
| ACAGAGATGCACTGAGATAtt | SEQ ID NO: 8 |
| AGGAAATACTACAGAGTGTtt | SEQ ID NO: 9 |
| GGCAAATACTCCTGTAAATtt | SEQ ID NO: 10 |
| CATTGAAAGTAAACAGAGAtt | SEQ ID NO: 11 |
| CCTGTAAATTTGAGTGTGAtt | SEQ ID NO: 12 |
| CAACAATACCCGAGAGTAGtt | SEQ ID NO: 13 |
| GAATGAAACTCTCAGATCAtt | SEQ ID NO: 14 |
| AAATGAAGATCCTGTGGTAtt | SEQ ID NO: 15 |
| GTGTGAACCAAGAGATATTtt | SEQ ID NO: 16 |
| CTACAGAGATGCACTGAGAtt | SEQ ID NO: 17 |
| ATGAAGATCCTGTGGTATTtt | SEQ ID NO: 18 |
| GTTTATGCATCCTTAGTTAtt | SEQ ID NO: 19 |
| TCTAAATACTCTTGCAGATtt | SEQ ID NO: 20 |
| GTGAGCAAGTTCTGAAAGAtt | SEQ ID NO: 21 |
| TGGCTAAGGAACTGGAAAAtt | SEQ ID NO: 22 |
| AAGAAGCAGTCTACAGCTAtt | SEQ ID NO: 23 |
| GAAAGTAAACAGAGATTTGtt | SEQ ID NO: 24 |
| CTAAGGAACTGGAAAATGAtt | SEQ ID NO: 25 |
| ACAACATGCTGCAGCTGTAtt | SEQ ID NO: 26 |
| CTGATGTATTTGAAGAAGAtt | SEQ ID NO: 27 |

TABLE 13-continued

Candidate DENND1B siRNA Molecules (sense)

| | |
|---|---|
| AGGCAAATCCAGACAGAACtt | SEQ ID NO: 28 |
| GTAAACAGAGATTTGGATTtt | SEQ ID NO: 29 |
| TTGCAGATTACTTGGCTAAtt | SEQ ID NO: 30 |
| ACCCAGTACCAAAGGCAAAtt | SEQ ID NO: 31 |
| AGGCAAATACTCCTGTAAAtt | SEQ ID NO: 32 |
| GCAAATACTCCTGTAAATTtt | SEQ ID NO: 33 |
| CATGAAAGGCGCATCGTGAtt | SEQ ID NO: 34 |
| GGAATACACTCCAGCCTCAtt | SEQ ID NO: 35 |
| CATTTAGTGACTTGAACAAtt | SEQ ID NO: 36 |
| TGTTGAAAGTGAAATGTCAtt | SEQ ID NO: 37 |
| CCTGTGGTATTGTGGAAATtt | SEQ ID NO: 38 |
| GGACCAAGGCAAATCCAGAtt | SEQ ID NO: 39 |
| AGACAGAACCTTTGACTTGtt | SEQ ID NO: 40 |
| CCTTTGACTTGGTGTTGAAtt | SEQ ID NO: 41 |
| TGCCATACCTGATTGGAATtt | SEQ ID NO: 42 |
| TGGAAGATGTTGTTATGTTtt | SEQ ID NO: 43 |
| AGAGATGCACTGAGATACAtt | SEQ ID NO: 44 |
| TGGCTTTTGTGGAGGTAAAtt | SEQ ID NO: 45 |
| GAATCAAGTTGGACAGCACtt | SEQ ID NO: 46 |
| ACAAATCATTGGAAGATGTtt | SEQ ID NO: 47 |
| GGACTTTGGAGACCAGGAtt | SEQ ID NO: 48 |
| ACTTTGGAGACCAGGAAATtt | SEQ ID NO: 49 |
| TGAAAGGGTGTCTCAGAATtt | SEQ ID NO: 50 |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A solid support having affixed thereon a collection of single nucleotide polymorphism (SNP)-containing isolated nucleic acids wherein each nucleic acid of the collection is at least 15 nucleotides in length, wherein the collection includes each allele of the SNPs, said SNPs being associated with an altered risk of developing pediatric onset asthma and consisting of
rs2786098, rs2821106, rs12134409, rs2111931, rs10737692, rs12127378, rs12041661, rs10442656, rs2477070, rs1747827, rs2488411, rs1891497, rs1747815, rs1775454, rs1775456, rs1924518, rs1775444, rs12026183, rs10922300, rs10922326, rs2821125, rs1337168, rs1337167, rs2786101, rs2821116, rs2786119rs2786117, rs10801603, rs2821107, rs2759656, rs2821103, rs2759661, rs2476019, rs2821132, rs17554990, rs6685222, rs17555558, rs10922234, rs12023045, rs12563307, rs12133659rs12132165, rs4915550, rs4915551, rs4915552, rs10754224, rs4316386, rs10922251, rs6677361, rs12028758, rs10922253, rs10494758, rs2111931, rs1421397, rs6689216, rs10922255, rs10922256, rs10922257, rs6676073, rs10737692, rs4915555, rs12131160, rs2193734, rs8179369, rs12747786, rs6428411, rs6428412, rs1833464, rs1362939, rs12116508, rs4915557, rs4915558, rs3814321, rs12133885, rs1775453, rs2488409, rs2488410, rs1775450, rs1747811, rs1578720, rs2358774, rs1573098, rs1621898, rs1775457, rs2147300, rs2488387, rs1747815, rs1747814, rs2488400, rs1747817, rs1775441, rs1775442, rs1342696, rs1539413, rs2488394, rs2488395, rs2488396, rs1342694, rs2477069, rs1775469, rs1747825, rs1775468, rs1775467, rs1775466, rs1775465, rs1775464, rs1747823, rs2454640, rs1499593, rs10922288, rs12740849, rs2133536, rs12125742, rs4915566, rs6428417, rs10922294, rs6697696, rs6704186, rs4915569, rs12140293, rs12118454, rs10801625, rs10922304, rs10922305, rs1499602, rs10801629, rs10801632, and rs9662705, wherein said isolated SNP-containing nucleic acids are immobilized on a gene chip or a solid support.

2. The isolated collection of nucleic acids as claimed in claim 1, wherein said solid support is a microarray and is present in a kit.

3. The kit of claim 2, comprising said microarray, a sample container, and reagents for analyzing a polynucleotide sample obtained from a subject, wherein the nucleic acids of the collection are probes between 15-25 nucleotides in length.

* * * * *

SEQUENCE LISTING

```
<160> NUMBER OF SEQ ID NOS: 50

<210> SEQ ID NO 1
<211> LENGTH: 21
<212> TYPE: DNA
<213> ORGANISM: Artificial Sequence
<220> FEATURE:
<223> OTHER INFORMATION: siRNA

<400> SEQUENCE: 1
tgacagacat tgaaagtaat t                                          21

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
cctcatagag agagtgaaat t                                          21

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
gtgattatct cgagcaaatt t                                          21

<210> SEQ ID NO 4
<211> LENGTH: 21
<212> TYPE: DNA
<213> ORGANISM: Artificial Sequence
<220> FEATURE:
<223> OTHER INFORMATION: siRNA
```

```
<400> SEQUENCE: 4
ggaagatgtt gttatgttat t                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gctcaagcgt gatgaaacat t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA

<400> SEQUENCE: 6
gagtgtgaac caagagatat t                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA

<400> SEQUENCE: 7
gagtagaaat cttacagaat t                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA

<400> SEQUENCE: 8
acagagatgc actgagatat t                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
aggaaatact acagagtgtt t                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
ggcaaatact cctgtaaatt t                                              21

<210> SEQ ID NO 11
```

```
<211> LENGTH: 21
<212> TYPE: DNA
<213> ORGANISM: Artificial Sequence
<220> FEATURE:
<223> OTHER INFORMATION: siRNA

<400> SEQUENCE: 11
cattgaaagt aaacagagat t                                               21

<210> SEQ ID NO 12
<211> LENGTH: 21
<212> TYPE: DNA
<213> ORGANISM: Artificial Sequence
<220> FEATURE:
<223> OTHER INFORMATION: siRNA

<400> SEQUENCE: 12
cctgtaaatt tgagtgtgat t                                               21

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
caacaatacc cgagagtagt t                                               21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
gaatgaaact ctcagatcat t                                               21

<210> SEQ ID NO 15
<211> LENGTH: 21
<212> TYPE: DNA
<213> ORGANISM: Artificial Sequence
<220> FEATURE:
<223> OTHER INFORMATION: siRNA

<400> SEQUENCE: 15
aaatgaagat cctgtggtat t                                               21

<210> SEQ ID NO 16
<211> LENGTH: 21
<212> TYPE: DNA
<213> ORGANISM: Artificial Sequence
<220> FEATURE:
<223> OTHER INFORMATION: siRNA

<400> SEQUENCE: 16
gtgtgaacca agagatattt t                                               21

<210> SEQ ID NO 17
<211> LENGTH: 21
<212> TYPE: DNA
<213> ORGANISM: Artificial Sequence
<220> FEATURE:
<223> OTHER INFORMATION: siRNA

<400> SEQUENCE: 17
```

```
ctacagagat gcactgagat t                                              21
```

<210> SEQ ID NO 18
<211> LENGTH: 21
<212> TYPE: DNA
<213> ORGANISM: Artificial Sequence
<220> FEATURE:
<223> OTHER INFORMATION: siRNA

<400> SEQUENCE: 18

```
atgaagatcc tgtggtattt t                                              21
```

<210> SEQ ID NO 19
<211> LENGTH: 21
<212> TYPE: DNA
<213> ORGANISM: Artificial Sequence
<220> FEATURE:
<223> OTHER INFORMATION: siRNA

<400> SEQUENCE: 19

```
gtttatgcat ccttagttat t                                              21
```

<210> SEQ ID NO 20
<211> LENGTH: 21
<212> TYPE: DNA
<213> ORGANISM: Artificial Sequence
<220> FEATURE:
<223> OTHER INFORMATION: siRNA

<400> SEQUENCE: 20

```
tctaaatact cttgcagatt t                                              21
```

<210> SEQ ID NO 21
<211> LENGTH: 21
<212> TYPE: DNA
<213> ORGANISM: Artificial Sequence
<220> FEATURE:
<223> OTHER INFORMATION: siRNA

<400> SEQUENCE: 21

```
gtgagcaagt tctgaaagat t                                              21
```

<210> SEQ ID NO 22
<211> LENGTH: 21
<212> TYPE: DNA
<213> ORGANISM: Artificial Sequence
<220> FEATURE:
<223> OTHER INFORMATION: siRNA

<400> SEQUENCE: 22

```
tggctaagga actggaaaat t                                              21
```

<210> SEQ ID NO 23
<211> LENGTH: 21
<212> TYPE: DNA
<213> ORGANISM: Artificial Sequence
<220> FEATURE:
<223> OTHER INFORMATION: siRNA

<400> SEQUENCE: 23

```
aagaagcagt ctacagctat t                                              21
```

<210> SEQ ID NO 24
<211> LENGTH: 21
<212> TYPE: DNA

```
<213> ORGANISM: Artificial Sequence
<220> FEATURE:
<223> OTHER INFORMATION: siRNA

<400> SEQUENCE: 24
gaaagtaaac agagatttgt t                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA

<400> SEQUENCE: 25
ctaaggaact ggaaaatgat t                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA

<400> SEQUENCE: 26
acaacatgct gcagctgtat t                                              21

<210> SEQ ID NO 27
<211> LENGTH: 21
<212> TYPE: DNA
<213> ORGANISM: Artificial Sequence
<220> FEATURE:
<223> OTHER INFORMATION: siRNA

<400> SEQUENCE: 27
ctgatgtatt tgaagaagat t                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA

<400> SEQUENCE: 28
aggcaaatcc agacagaact t                                              21

<210> SEQ ID NO 29
<211> LENGTH: 21
<212> TYPE: DNA
<213> ORGANISM: Artificial Sequence
<220> FEATURE:
<223> OTHER INFORMATION: siRNA

<400> SEQUENCE: 29
gtaaacagag atttggattt t                                              21

<210> SEQ ID NO 30
<211> LENGTH: 21
<212> TYPE: DNA
<213> ORGANISM: Artificial Sequence
<220> FEATURE:
<223> OTHER INFORMATION: siRNA

<400> SEQUENCE: 30
ttgcagatta cttggctaat t                                              21
```

<210> SEQ ID NO 31
<211> LENGTH: 21
<212> TYPE: DNA
<213> ORGANISM: Artificial Sequence
<220> FEATURE:
<223> OTHER INFORMATION: siRNA

<400> SEQUENCE: 31
acccagtacc aaaggcaaat t                                                21

<210> SEQ ID NO 32
<211> LENGTH: 21
<212> TYPE: DNA
<213> ORGANISM: Artificial Sequence
<220> FEATURE:
<223> OTHER INFORMATION: siRNA

<400> SEQUENCE: 32
aggcaaatac tcctgtaaat t                                                21

<210> SEQ ID NO 33
<211> LENGTH: 21
<212> TYPE: DNA
<213> ORGANISM: Artificial Sequence
<220> FEATURE:
<223> OTHER INFORMATION: siRNA

<400> SEQUENCE: 33
gcaaatactc ctgtaaattt t                                                21

<210> SEQ ID NO 34
<211> LENGTH: 21
<212> TYPE: DNA
<213> ORGANISM: Artificial Sequence
<220> FEATURE:
<223> OTHER INFORMATION: siRNA

<400> SEQUENCE: 34
catgaaaggc gcatcgtgat t                                                21

<210> SEQ ID NO 35
<211> LENGTH: 21
<212> TYPE: DNA
<213> ORGANISM: Artificial Sequence
<220> FEATURE:
<223> OTHER INFORMATION: siRNA

<400> SEQUENCE: 35
ggaatacact ccagcctcat t                                                21

<210> SEQ ID NO 36
<211> LENGTH: 21
<212> TYPE: DNA
<213> ORGANISM: Artificial Sequence
<220> FEATURE:
<223> OTHER INFORMATION: siRNA

<400> SEQUENCE: 36
catttagtga cttgaacaat t                                                21

<210> SEQ ID NO 37
<211> LENGTH: 21
<212> TYPE: DNA
<213> ORGANISM: Artificial Sequence
<220> FEATURE:

<223> OTHER INFORMATION: siRNA

<400> SEQUENCE: 37
tgttgaaagt gaaatgtcat t                                              21

<210> SEQ ID NO 38
<211> LENGTH: 21
<212> TYPE: DNA
<213> ORGANISM: Artificial Sequence
<220> FEATURE:
<223> OTHER INFORMATION: siRNA

<400> SEQUENCE: 38
cctgtggtat tgtggaaatt t                                              21

<210> SEQ ID NO 39
<211> LENGTH: 21
<212> TYPE: DNA
<213> ORGANISM: Artificial Sequence
<220> FEATURE:
<223> OTHER INFORMATION: siRNA

<400> SEQUENCE: 39
ggaccaaggc aaatccagat t                                              21

<210> SEQ ID NO 40
<211> LENGTH: 21
<212> TYPE: DNA
<213> ORGANISM: Artificial Sequence
<220> FEATURE:
<223> OTHER INFORMATION: siRNA

<400> SEQUENCE: 40
agacagaacc tttgacttgt t                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA

<400> SEQUENCE: 41
cctttgactt ggtgttgaat t                                              21

<210> SEQ ID NO 42
<211> LENGTH: 21
<212> TYPE: DNA
<213> ORGANISM: Artificial Sequence
<220> FEATURE:
<223> OTHER INFORMATION: siRNA

<400> SEQUENCE: 42
tgccatacct gattggaatt t                                              21

<210> SEQ ID NO 43
<211> LENGTH: 21
<212> TYPE: DNA
<213> ORGANISM: Artificial Sequence
<220> FEATURE:
<223> OTHER INFORMATION: siRNA

```
<400> SEQUENCE: 43
tggaagatgt tgttatgttt t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA

<400> SEQUENCE: 44
agagatgcac tgagatacat t                                              21

<210> SEQ ID NO 45
<211> LENGTH: 21
<212> TYPE: DNA
<213> ORGANISM: Artificial Sequence
<220> FEATURE:
<223> OTHER INFORMATION: siRNA

<400> SEQUENCE: 45
tggcttttgt ggaggtaaat t                                              21

<210> SEQ ID NO 46
<211> LENGTH: 21
<212> TYPE: DNA
<213> ORGANISM: Artificial Sequence
<220> FEATURE:
<223> OTHER INFORMATION: siRNA

<400> SEQUENCE: 46
gaatcaagtt ggacagcact t                                              21

<210> SEQ ID NO 47
<211> LENGTH: 21
<212> TYPE: DNA
<213> ORGANISM: Artificial Sequence
<220> FEATURE:
<223> OTHER INFORMATION: siRNA

<400> SEQUENCE: 47
acaaatcatt ggaagatgtt t                                              21

<210> SEQ ID NO 48
<211> LENGTH: 21
<212> TYPE: DNA
<213> ORGANISM: Artificial Sequence
<220> FEATURE:
<223> OTHER INFORMATION: siRNA

<400> SEQUENCE: 48
ggactttgga gaccaggaat t                                              21

<210> SEQ ID NO 49
<211> LENGTH: 21
<212> TYPE: DNA
<213> ORGANISM: Artificial Sequence
<220> FEATURE:
<223> OTHER INFORMATION: siRNA

<400> SEQUENCE: 49
actttggaga ccaggaaatt t                                              21

<210> SEQ ID NO 50
```

```
<211> LENGTH: 21
<212> TYPE: DNA
<213> ORGANISM: Artificial Sequence
<220> FEATURE:
<223> OTHER INFORMATION: siRNA

<400> SEQUENCE: 50
tgaaagggtg tctcagaatt t                                              21
```